(12) United States Patent
McKinney, IV et al.

(10) Patent No.: US 11,170,892 B1
(45) Date of Patent: Nov. 9, 2021

(54) METHODS AND SYSTEMS FOR ANALYSIS OF REQUESTS FOR RADIOLOGICAL IMAGING EXAMINATIONS

(71) Applicant: VEEV, Inc., New Brighton, MN (US)

(72) Inventors: Alexander Marcellus Preston McKinney, IV, New Brighton, MN (US); Zeke Jordan McKinney, Minneapolis, MN (US); Kevin Donald Campbell, Minneapolis, MN (US)

(73) Assignee: Veev, Inc., New Brighton, MN (US)

( * ) Notice: Subject to any disclaimer, the term of this patent is extended or adjusted under 35 U.S.C. 154(b) by 141 days.

(21) Appl. No.: 16/211,347

(22) Filed: Dec. 6, 2018

(51) Int. Cl.
 *G16H 40/20* (2018.01)
 *G16H 30/40* (2018.01)

(52) U.S. Cl.
 CPC ............. *G16H 40/20* (2018.01); *G16H 30/40* (2018.01)

(58) Field of Classification Search
 None
 See application file for complete search history.

(56) References Cited

U.S. PATENT DOCUMENTS

| | | | |
|---|---|---|---|
| 6,292,771 B1 | 9/2001 | Haug et al. | |
| 6,915,254 B1 | 7/2005 | Heinze et al. | |
| 8,782,088 B2 | 7/2014 | Carus et al. | |
| 8,935,155 B2 | 1/2015 | Bretschneider et al. | |
| 9,152,763 B2 | 10/2015 | Carus et al. | |
| 2007/0067185 A1 | 3/2007 | Halsted | |
| 2008/0004505 A1 | 1/2008 | Kapit | |
| 2009/0192822 A1 | 7/2009 | Regulapati et al. | |
| 2010/0256459 A1 | 10/2010 | Miyasa et al. | |
| 2013/0103425 A1* | 4/2013 | Julsrud | G16H 30/20 705/3 |
| 2014/0317080 A1 | 10/2014 | Piraino et al. | |
| 2015/0066539 A1 | 3/2015 | Sheffer et al. | |
| 2015/0379241 A1 | 12/2015 | Furst | |
| 2016/0239564 A1 | 8/2016 | Sohma | |
| 2016/0350497 A1* | 12/2016 | Hashoul | G06F 19/00 |
| 2017/0235888 A1 | 8/2017 | Rahman et al. | |
| 2018/0373844 A1 | 12/2018 | Ferrandez-Escamez et al. | |
| 2019/0108175 A1* | 4/2019 | Sevenster | G06F 40/289 |
| 2020/0027534 A1* | 1/2020 | Chang | G16H 15/00 |

OTHER PUBLICATIONS

Petro, J., Natural Language Processing in Health Records, retrieved on Jan. 31, 2017 from http://www.kevinmd.com/blog/2011/09/natural-language-processing-electronic-health-records.html.

(Continued)

*Primary Examiner* — Devin C Hein

(57) ABSTRACT

Methods for analysis of radiologic imaging orders including using a processor, executing instructions to perform the steps of receiving a query for analysis of radiologic imaging orders of a group of patients who underwent radiologic imaging exams resulting in radiologic exam reports, wherein the radiologic imaging exam orders were used to order the radiologic imaging exams, identifying reason for exam codes for the radiologic imaging orders, identifying exam report diagnosis codes for the radiologic exam reports, calculating a value for a correlation between the reason for exam codes and the exam report diagnosis codes, and comparing the calculated value to a standard.

20 Claims, 5 Drawing Sheets

(56) References Cited

OTHER PUBLICATIONS

Pons, E., Natural Language Processing in Radiology: A Systematic Review, Radiology, vol. 279, No. 2, May 2016.
Payabvash, S., Screening and Detection of Blunt Vertebral Artery Injury in Patients with Upper Cervical Fractures: The Role of Cervical CT and CT Angiography, European Journal of Radiology, 2013.
Farkas, R., Automatic Construction of Rule-Based ICD-9-CM Coding Systems, BMC Bioinformatics, Apr. 11, 2008, vol. 9, Supplement 3, S10.

* cited by examiner

See full report data for Study ID:990555780.
Impression Line: 2 Head CTA demonstrates no evident arterial injury, aneurysm, or stenosis of the major intracranial arteries. ← 502

Diagnoses matching negative phrase: evident arterial injury aneurysm stenosis major posterior cerebral arteries anterior cerebral arteries posterior communicating arteries posterior cerebellar arteries anterior inferior cerebellar arteries posterior inferior cerebellar arteries internal carotid arteries basilar artery
Search results: 199 distinct combinations of matching words for this phrase found.
Search results: 3446 best diagnoses per distinct combination of matching words for this phrase found, showing the first 10.
Note matches with same best score are included for same distinct combination of matching words.

| ICD-10 Code | ICD Filter Category | Diagnosis Name | Num Diagnosis Words | Number of Matching Words (including duplicates) | Match Factor | Subtract Factor | Order Factor | Score | Word Matches |
|---|---|---|---|---|---|---|---|---|---|
| I65.23 | Head/Neuro | Stenosis of both internal carotid arteries | 4 | 4 | 2.3007 | 1.0000 | 1.3 | 11.9636 | arteries,carotid,internal,stenosis |
| I66.03 | Head/Neuro | Stenosis of both middle cerebral arteries | 4 | 4 | 2.0721 | 1.0000 | 1.4 | 11.6041 | arteries,cerebral,middle,stenosis |
| I67.1 | Head/Neuro | Anterior communicating artery aneurysm | 4 | 4 | 2.5406 | 1.0000 | 1.1 | 11.1786 | aneurysm,anterior,artery,communicating |
| I67.1 | Head/Neuro | Posterior communicating artery aneurysm | 4 | 4 | 2.5396 | 1.0000 | 1.1 | 11.1479 | aneurysm,artery,communicating,posterior |
| I65.29 | Head/Neuro | Internal carotid artery stenosis | 4 | 4 | 1.8820 | 1.0000 | 1.1 | 8.2810 | artery,carotid,internal,stenosis |
| I68.8 | Head/Neuro | Ruptured aneurysm of posterior cerebellar artery | 6 | 5 | 2.4092 | 0.8337 | 1.2 | 8.3267 | aneurysm,artery,cerebellar,inferior,posterior |
| I67.1 | Head/Neuro | Aneurysm of middle cerebral artery | 4 | 4 | 1.7710 | 1.0000 | 1.1 | 7.7925 | aneurysm,artery,cerebral,middle |
| I67.1 | Head/Neuro | Aneurysm of anterior cerebral artery | 4 | 4 | 1.7547 | 1.0000 | 1.1 | 7.7239 | aneurysm,anterior,artery,cerebral |
| I67.1 | Head/Neuro | Aneurysm of posterior cerebral artery | 4 | 4 | 1.7478 | 1.0000 | 1.1 | 7.6903 | aneurysm,artery,cerebral,posterior |
| S15.009A | Head/Neuro | Internal carotid artery injury | 4 | 4 | 1.7146 | 1.0000 | 1.1 | 7.5445 | artery,carotid,injury,internal |

FIG. 5

METHODS AND SYSTEMS FOR ANALYSIS OF REQUESTS FOR RADIOLOGICAL IMAGING EXAMINATIONS

BACKGROUND

As healthcare costs continue to rise, there are increasing efforts by the government, insurers, health care providers and patients themselves to curb this upward trend while maintaining quality care. While health care is an essential need, the rising costs make it difficult to provide health care coverage at the same levels as in the past. New techniques are therefore needed to identify and eliminate needless expenses within the health care system, particularly if such techniques can be implemented at minimal cost.

One of the areas targeted most by the Federal government for cost control measures is radiology, since radiologic imaging exams carry a significant cost. Radiologic imaging exams are tremendously powerful tools that enable nearly immediate monitoring and diagnosis of medical conditions. The ability to noninvasively visualize inside a patient's body is sometimes the only way to diagnose a condition and can be done with minimal impact upon the patient. However, it is exactly because radiological exams are so powerful that they are at risk for overuse by ordering physicians. In this difficult time of rising health care costs, it is more important than ever that radiologic imaging exams be ordered carefully and appropriately.

Ordering physicians may commit several types of errors when ordering radiologic imaging exams. They may simply select the wrong type of radiologic imaging exam for the condition they are attempting to diagnose or rule out. More likely, they may order a medical imaging exam prematurely, such as before performing other less expensive tests or other steps which could provide a diagnosis and therefore eliminate the need for the medical imaging exam in some cases. In such cases, the radiologic imaging exam may be a correct exam for a particular diagnosis, but it is at risk for being overused. In still other cases, the ordering physician may make an error in submitting the reason for the examination with the order for the examination, and the charges for the exam may not be paid by insurance as a result.

Various systems exist to help steer ordering physicians toward the appropriate use of radiologic imaging exams. For example, when inputting the order into a computerized order system, the system may include alerts or requests for further information when certain exams are ordered to help prevent errors. For example, when an order for a radiologic imaging exam is entered into an order system, the ordering system may pop up further information to alert the ordering physician to clinical situations in which the exam is or is not appropriate. Alternatively, the ordering system may request further information about the clinical situation to determine whether the exam is likely appropriate or not and may alert the ordering physician to its conclusions. However, because each situation is unique, the ordering system typically will not prevent a physician from ordering a radiologic imaging exam even if the ordering system concludes that the exam is inappropriate, because the ordering physician has advanced training, knows the complete medical situation and makes the ultimate decision regarding what tests to perform. The ordering physician is therefore ultimately responsible for making the correct decision regarding the use of radiologic imaging exams.

In some situations, the members of the radiology department may provide a check on the inappropriate use of a radiologic imaging exam. When an ordering physician completes an order for a radiologic imaging exam, the order may include a brief description of the patient's clinical history. The order may also include an alphanumeric code, such as an ICD-10 code and corresponding verbal description, as the reason for exam. The ordering system may require the ordering physician to input this reason for exam in order to complete the order. If the patient's history and/or reason for exam are not consistent with the type of radiologic imaging exam to be performed, a member of the radiology department may contact the ordering physician to discuss the matter further and the type of radiologic imaging exam may be changed, the characteristics of the radiologic imaging exam may be modified (such as the whether or not contrast is used), or the radiologic imaging exam may be cancelled. However, this type of check relies upon human diligence and requires significant time and may therefore only occur on an intermittent basis, and as a result may only avert inappropriate radiologic imaging exams periodically.

While such methods seem likely to decrease the misuse of radiological imaging exams, some errors are still likely to occur. Human review on a case-by-case basis can be overly time consuming and can still permit ordering errors. Improvements are therefore needed to detect and reduce the inappropriate use of radiologic imaging exams.

SUMMARY

Various embodiments include computer implemented methods for analysis of radiologic imaging orders. The methods include using a processor, executing computer readable instructions stored in non-transitory computer readable media to perform the steps of receiving a query for analysis of radiologic imaging orders of a group of patients who underwent radiologic imaging exams resulting in radiologic exam reports, wherein the radiologic imaging exam orders were used to order the radiologic imaging exams, identifying reason for exam codes for the radiologic imaging orders, identifying exam report diagnosis codes for the radiologic exam reports, calculating a value for a correlation between the reason for exam codes and the exam report diagnosis codes, and comparing the calculated value to a standard. The standard may be a threshold value. The value for the correlation between the reason for exam codes and the exam report diagnosis codes may be a frequency with which one reason for exam code was associated with one exam report diagnosis code within the group of patients. The value for the correlation between the reason for exam codes and the exam report diagnosis codes may be a frequency with which one or more particular reason for exam codes present on radiologic imaging exams resulted in one or more particular exam report diagnosis codes within the group of patients.

In some embodiments, for one or more of the radiologic imaging exam reports, identifying exam report diagnosis codes in radiologic exam reports includes segmenting the radiologic exam report into a plurality of units of text, comparing a first unit of text to a plurality of phrases contained in a database to identify one or more matched phrases, wherein a matched phrase is identified when a phrase in the database has one or more words that are the same as one or more words in the first modified unit of text, and repeating these steps for a second unit of text.

In some embodiments, receiving a query includes receiving a query from a user, and the method further includes, based on the comparison, notifying the user of an actual problem or a potential problem with the radiologic imaging exam orders for the group of patients, wherein the actual problem or the potential problem comprises over utilization of a radiologic imaging exam type or ordering incorrect radiologic imaging exams within the radiologic exams performed on the group of patients.

In other embodiments includes the method includes, using a processor, executing computer readable instructions stored in non-transitory computer readable media to perform the steps of receiving a query for analysis of radiologic imaging orders of a group of patients who underwent radiologic imaging exams resulting in radiologic exam reports, wherein the radiologic imaging exam orders were used to order the radiologic imaging exams, identifying reason for exam codes for the radiologic imaging orders, identifying exam report diagnosis codes for the radiologic exam reports by performing the steps of segmenting the radiologic exam report into a plurality of units of text, comparing a first unit of text to a plurality of phrases contained in a database to identify one or more matched phrases, wherein a matched phrase is identified when a phrase in the database has one or more words that are the same as one or more words in the first modified unit of text, and repeating these steps for a second unit of text, and calculating a value for a correlation between one or more reason for exam codes and one or more exam report diagnosis codes. In some embodiments, the method includes comparing the calculated value a standard to determine if the calculated value is greater than, equal to or less than the standard.

In some embodiments, the value for the correlation between the reason for exam codes and the exam report diagnosis codes may be a frequency with which one or more particular reason for exam codes present on radiologic imaging exams which resulted in one or more particular exam report diagnosis codes within the group of patients.

In some embodiments, receiving a query includes receiving a query from a user, and the method further includes providing a result to the user. The method may also include notifying the user of an actual problem or a potential problem with the radiologic imaging exam orders for the group of patients. For example, the actual problem or the potential problem may include over utilization of a radiologic imaging exam type or ordering incorrect radiologic imaging exams.

In other embodiments, the method includes using a processor, executing computer readable instructions stored in non-transitory computer readable media to perform the steps of receiving a query from a user for analysis of radiologic imaging orders of a group of patients who underwent radiologic imaging exams resulting in radiologic exam reports, wherein the radiologic imaging exam orders were used to order the radiologic imaging exams, identifying reason for exam codes for the radiologic imaging orders, identifying exam report diagnosis codes for the radiologic exam reports, calculating a value for a correlation between the reason for exam codes and the exam report diagnosis codes, comparing the calculated value to a standard, and based on the comparison, notifying the user of whether or not there is an actual problem or a potential problem with the radiologic imaging exam orders for the group of patients. The actual problem or the potential problem may be over utilization of a radiologic imaging exam type within the radiologic exams performed on the group of patients or ordering incorrect radiologic imaging exams within the radiologic exams performed on the group of patients, for example.

In some embodiments, the step of identifying exam report diagnosis codes for the radiologic exam reports includes performing segmenting the radiologic exam report into a plurality of units of text, comparing a first unit of text to a plurality of phrases contained in a database to identify one or more matched phrases, wherein a matched phrase is identified when a phrase in the database has one or more words that are the same as one or more words in the first modified unit of text, and repeating these steps for a second unit of text. These steps may be performed by the processor in response to the query or may be performed prior to the query, either by the processor or by a second processor, and the resulting exam result codes resulting may be stored in digital memory and accessed by the processor for use in the steps of the method.

BRIEF DESCRIPTION OF THE DRAWINGS

The following drawings are illustrative of particular embodiments and do not limit the scope of the inventions. The drawings are not necessarily to scale and are intended for use in conjunction with the following detailed description. Embodiments of the inventions will be described with reference to the drawings, in which like numerals may represent like elements.

FIG. 5 is an example of a user display of a list of matched diagnoses for a unit of text from a report for an example report analysis system.

DETAILED DESCRIPTION

Figure 1:
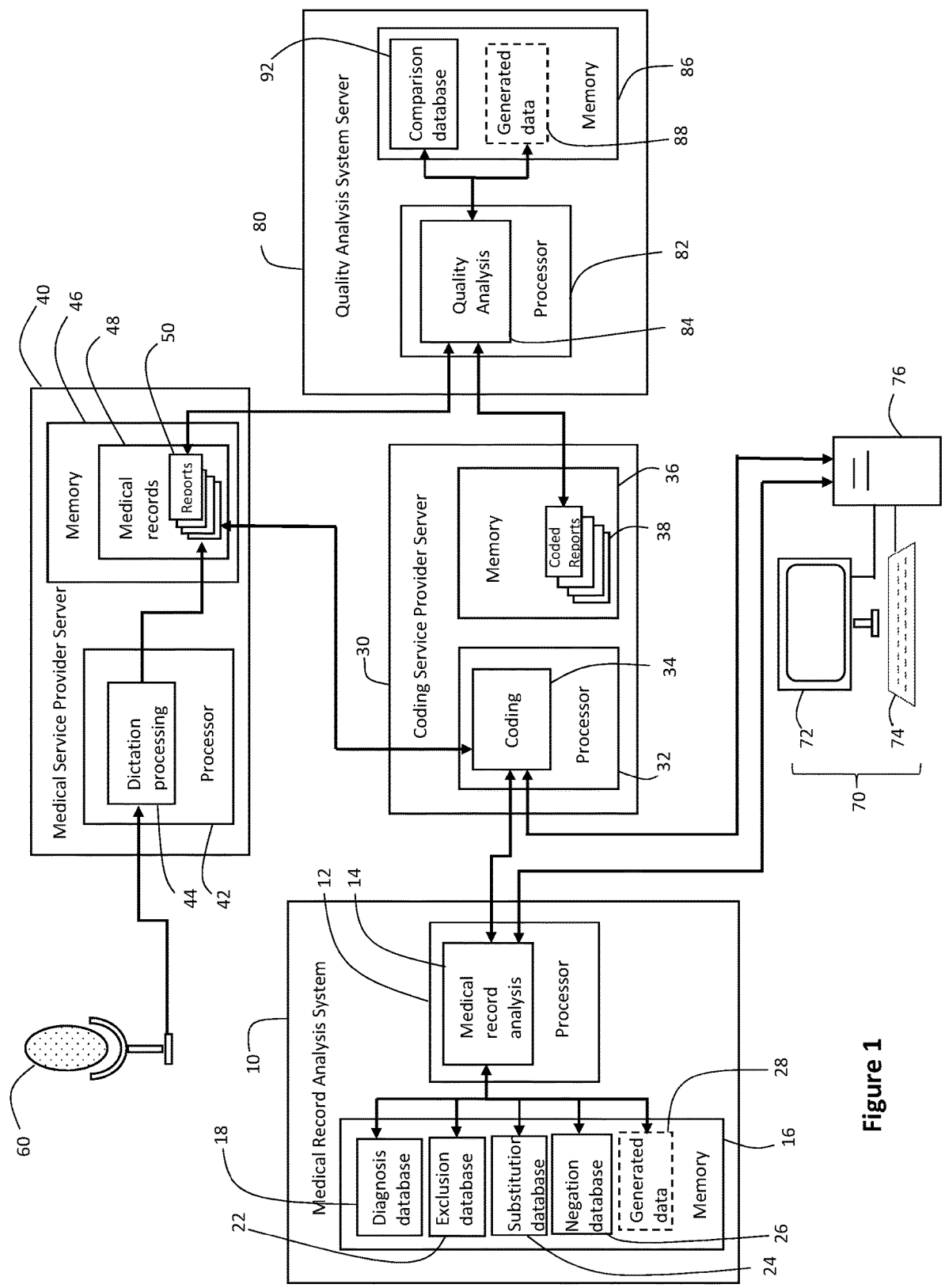
FIG. 1 is a system for quality analysis of the ordering of radiologic imaging exams.

The following detailed description is exemplary in nature and is not intended to limit the scope, applicability, or configuration of the inventions. Rather, the following description provides practical illustrations for implementing various exemplary embodiments. Utilizing the teachings provided herein, those skilled in the art may recognize that many of the examples have suitable alternatives that may be utilized.

Various embodiments provide systems and methods to compare the reasons for exam presented with the radiologic imaging exam order to the resulting imaging exam report diagnoses and/or the potential imaging encounter diagnosis. Using these comparisons, various types of potential ordering errors can be automatically detected. Users of the system can be alerted to the potential error so that corrections can be made to reduce such problems in the future, reducing the inappropriate use of radiologic imaging exams and associated wasted spending to help control health care costs.

Radiologic imaging exams used in various embodiments may be any type of radiologic image, including but not limited to X-ray, magnetic resonance imaging (MRI), magnetic resonance angiography (MRA), computed tomography (CT), CTA, fluoroscopy, mammography, nuclear medicine including bone scans, thyroid scans, and cardiac stress tests, positron emission tomography (PET) scans, and ultrasound reports, for example.

Many medical conditions require radiological imaging for diagnosis and/or for monitoring the condition. The process typically begins with a consultation with a physician (or physician's assistant or other medical professional) who, in response to a set of symptoms, laboratory results, previous radiological exams, family history, and/or other factors, orders a radiological imaging exam for the patient. This order is often entered into the computer system of the medical institution at which the consultation occurred, and may be automatically available to the appropriate radiology department, enabling the patient to receive the radiological exam. In order for the order to be complete and accepted by the medical institution, the radiology department, and/or public or private insurers, the radiological imaging order typically must include a "reason for exam." The order form may be completed and submitted by the ordering physician or other medical professional or by another individual working on behalf of the ordering physician. However, it should be understood that when this application refers to an "ordering physician" the phrase includes any medical provider ordering an exam, as well as those individuals (who may or may not be physicians) acting on behalf of the physician or other medical provider.

The "reason for exam" is selected and entered by the ordering physician. The format of the reason for exam depends upon the choice of the institution, among other things. The accepted format of the reason for exam may be free form plain text written by the ordering physician. Alternatively, the accepted format may be a plain text description selected from a predetermined list such as a drop down list. In increasingly common alternatives, the accepted format of the reason for exam may be an alphanumeric code which may be selected from a list such as a drop down list. The same or similar codes may be used for coding medical services in order to obtain reimbursement from Medicare and insurance providers. The radiologic imaging exam order may accept reasons for exam in only one format or in more than one format at the choice of the ordering physician.

Whatever the purpose of the alphanumeric code, when it is used for a reason for exam, an individual must identify the appropriate reason for exam (or in other circumstances, the appropriate diagnosis) as an alphanumeric code from a set of standardized codes such as the $10^{th}$ revision of the International Statistical Classification of Diseases and Related Health Problems (ICD-10), the current coding system used by medical service providers in the United States. However, given the complexity of the medical field and the need for accurate and specific information, such code systems are voluminous, with the ICD-10 code system including over 68,000 codes. As a result, the process of identifying the correct reasons for exams or diagnoses and the associated codes is time-consuming. In addition, given the vast number of codes, it can be difficult for people to identify the correct or most specific code.

Ordering physicians may make various types of mistakes when ordering radiologic imaging exams. Given the large number of diagnostic codes from which to choose, the process of ordering a radiologic imaging exam may be difficult and time consuming, and taking the time to carefully select the proper code, for example, may be a low priority. For this reason as well as others, an ordering physician may sometimes select an incorrect reason for exam. For example, an ordering physician may select a reason for exam code or select or enter a free text description which does not correspond to the actual reason for exam through simple human error. Alternatively, an ordering physician may select a reason for exam code or select or enter a free text description which is correct but is overly generic even though a more specific and therefore more accurate and more informative reason for exam was possible or existed.

In other cases, an ordering physician may select an incorrect type of radiologic imaging exam. As with selecting the wrong reason for exam code, an ordering physician may select the wrong type of radiologic imaging exam through simple human error by selecting the wrong type of exam while intending to pick the correct one. In other cases, the ordering physician may order the wrong type of radiologic imaging exam due to a lack of knowledge, failure to keep abreast of changing standards, or unfamiliarity with new or changing technology. For example, an ordering physician may select a type of radiologic imaging exam for the purpose of diagnosing a condition but the selected exam may not be effective, or may be less effective than an alternative type of radiologic imaging exam, for detecting that particular condition. Alternatively, an ordering physician may select a type of radiologic imaging exam for the purpose of diagnosing a medical condition, and the selected exam type may be effective for diagnosing that condition, but the exam may not be indicated for that patient at that time. For example, there may be other steps which should occur first, prior to ordering the imaging exam, in order to eliminate the possibility of other medical conditions. If these other steps are skipped, and if the physician orders the radiologic imaging exam prematurely, the ordering physician may be over utilizing the imaging exam.

In some cases, the ordering physician may fail to insert a reason for exam into the radiologic imaging exam order. In such cases, the radiologist performing the exam may have insufficient information to guide the performance of the exam or the interpretation of the results. In addition, payers such as insurers may refuse to pay for imaging exams when a reason for exam is not provided in the order.

Each of these types of ordering errors can result in increased costs, which must be paid by the insurer, the patient, and/or the medical services provider. In an effort to control medical costs, various training programs, automated checks, and other systems exist to attempt to prevent these types of error, but such errors continue to occur and can be difficult or impossible to detect using traditional methods. The various embodiments of the inventions described herein go beyond existing error prevention systems to detect errors that occur despite the existing systems.

Various embodiments of the inventions provide systems and methods for feedback analysis by comparing reason for exam codes to radiologic imaging exams result codes and/or to post-imaging encounter diagnosis for patients. In this way, errors in the ordering of radiologic imaging exams, including the use of incorrect reason for exam codes and incorrect types of examinations, can be detected so that remedial actions can be taken and medical expenses can be reduced in the future.

The exam result codes used for these comparisons may be determined based upon the results of the radiologic imaging exam. When a radiologist reviews a radiological study such as an X-ray or MRI, the radiologist typically dictates his or her findings into a report which includes a description of the study and the radiologist's observations and conclusions about normal and abnormal findings. Similar reports are dictated by physicians and other medical service providers in other areas of medicine such as pathology, cardiology, and other fields. The free form descriptions created by the physicians can be manually or automatically transcribed into written text and are full of useful information. In the clinical context, the reports may be read and easily understood by other physicians and medical service providers as part of the caregiving process.

The radiologic imaging exam report, or exam report, includes the radiologist's findings including the radiologist's conclusions regarding diagnoses (both present and absent) in the radiologic imaging exam. That is, the radiologic imaging exam report indicates the conditions which are present and, if relevant, also indicates the conditions which are absent, since some radiologic imaging exams are performed to specifically determine whether a condition is present or is absent, that is, to "rule out" the condition. These radiologic imaging exam reports are created using ordinary language, by a reading radiologist, rather than an alphanumeric code. As such, the downstream diagnosis from the radiologic imaging exam report may be obtained by converting the ordinary language of the exam report into an alphanumeric code.

The post-exam encounter occurs after the imaging exam and may be any activity which results in a diagnosis. Examples include follow up appointments, inpatient assessments, telephone calls, additional imaging examinations, or diagnostic/therapeutic procedures. In some cases, the post-exam encounter may include the creation of a report with one or more diagnoses, while in other cases it may simply include the creation of a diagnoses by a physician and may be in free text form and/or in an alphanumeric code. The post-exam encounter report and diagnoses are typically entered into the patient's medical record in the medical service provider's server and may be accessible to the quality analysis server system for performance of the analysis described herein.

Because exam reports are written in free form and can be complex, it may be helpful or necessary for people to read the exam reports to gather information from them, rather than gather the information automatically. In some embodiments of the invention, the diagnoses found in radiologic imaging exam reports may be converted into alphanumeric exam diagnosis codes by coders, such as for the purposes of reimbursement by insurers or major payers, such as Medicare. These coders are individuals who may read portions or all of the exam report to identify and input the diagnosis information from the exam report into a computerized system in a systematic format which the computerized system is able to use. The format of such codes may be an alphanumeric code such as an ICD-10 code. However, the process of human coding is laborious and there is a risk that coders may not select the codes most likely to affect the patient's outcome or most immediate symptoms, but rather those most likely to enable optimal reimbursement.

Alternatively, as computerized systems and electronic health records become more sophisticated, it is increasingly possible for such systems to automatically review free form text such as in a reason for exam, an exam report, and post-exam encounter diagnosis and identify or generate relevant alphanumeric codes. As such, in some embodiments of the invention, the system may automatically identify the alphanumeric codes for the diagnoses in the exam report (imaging exam report codes), or the most likely alphanumeric codes for the diagnoses in the exam report, using a report analysis system, for example. In other embodiments, the system may use a combination of human coders and automated review by a report analysis system to determine the diagnoses and associated alphanumeric codes. Similarly, when the encounter diagnosis is in free text form, the system may automatically identify an alphanumeric code for each post-exam encounter diagnosis, or the most likely alphanumeric code, using an encounter analysis system, for example, or may use a combination of human coders and automated review by an encounter analysis system to determine each post-exam encounter diagnosis and associated alphanumeric code. When the reason for exam is in free text form, the system may likewise automatically identify an alphanumeric code for each reason for exam.

In some cases, the post-exam encounter diagnoses may be entered by physicians in a systematic format that the system may use, such as the form of an alpha numeric code such as the ICD-10 code. In other cases, as with the exam results, coders may identify the appropriate codes for the post exam encounter diagnoses and/or the post exam encounters may be determined from the post exam encounter reports automatically or in combination with a coder.

Examples of such a medical record analysis systems which may be used in various embodiments for automatically identifying alphanumeric codes in medical records including codes for reasons for exam, exam report diagnoses, and post-exam encounter diagnosis, either independently or in combination with a human coder, are described in U.S. patent application Ser. No. 15/637,060, entitled Methods and Systems for Automatic Analysis of Medical Reports, the full disclosure of which is hereby incorporated by reference. While the system descried in this patent application is referred to as a report analysis system and relates specifically to the analysis of exam reports and the generation of exam report codes, the teachings of this application apply to the record analysis systems describe herein which may be used not only with exam reports but also with imaging exam orders and post-exam encounter reports. In addition, various examples of medical record analysis systems which may be used in various embodiments are described later in this application.

The codes used for (or obtained by the system based upon) the reasons for exam for ordering the radiological imaging exams, and the diagnoses codes for the radiologic imaging exam results, and the post-exam encounter diagnosis codes may be selected by an ordering physician or determined by the record analysis system and/or coder using standardized set of diagnoses which may include a list of specific diagnoses in normal language and the correlated alphanumeric code for each normal language diagnosis on the list. Examples of standardized sets of codes which may be used in various embodiments include the ICD-9 and ICD-10. The standardized set of codes may further include subtypes of diagnoses names and the associated numerical codes. The quality analysis system and methods described herein could also be used with other standardized sets of codes. While in some embodiments, the reason for exam code, the exam result code, and the post-exam encounter code may be codes from the same standardized set of codes, in other embodiments they may be from different standardized sets of codes.

After codes are obtained for the reason for exam, the imaging exam report, and/or the post-exam encounter, various comparisons can be made by the system to detect potential problems. For example, after an imaging exam diagnosis code is obtained from an imaging exam report, whether by a human such as a coder, automatically by a computerized system, or a combination of a human and computerized system, the imaging exam report code may be compared to the reason for exam code. This comparison can be used to suggest, on a case by case basis, whether the radiologic imaging exam may have been the correct type of exam for the reason for exam or whether it may have been incorrect. On a larger scale, such as a group of patients, this comparison can suggest whether there may be a trend of problems with the selection of the reason for exam or with the type of radiologic imaging exam ordered. For example, the group may be a group of patients all of whom received a particular type of radiologic imaging exam. This group may be further identified or defined by geographic location (such as one or more city, state, zip code of the patient or provider, or location of care such as a hospital or other institution), clinical provider or providers (such as one or more individual reading radiologists, ordering clinicians, physician groups), and/or type of imaging study or studies. For example, the group of patients may be all patients having a particular ordering physician, or an ordering physician within a particular group of physicians, medical institution, etc. The ordering history of any individual or group may be selected and evaluated in this way. As such, an insurer or other payer (for the imaging examination) may adjust reimbursement to an individual physician or group accordingly, based on such trends.

The type of information obtained from an imaging exam varies depending upon the clinical situation and the type of imaging exam performed, therefore, there is no single result which can be expected. Because of this, the expected results for the comparison of a reason for exam code to an imaging exam report code will vary depending upon many factors. In some cases, for an appropriately ordered exam, the reason for exam code may be expected to be consistent with the reason for exam code, while in other cases, they would not be expected to be consistent. For example, certain reason for exam codes for certain imaging exams may be commonly associated with certain likely imaging result findings and therefore with a set of likely possible imaging exam report codes. Some of these associated imaging exam report codes may indicate that the imaging exam was proper for the patient, while others may be neutral, and still others may indicate that it was likely not a proper imaging exam for that patient. Furthermore, again depending upon the reason for exam code and the type of imaging exam, it may be expected that a certain proportion of imaging exams do not result in an imaging exam report code which indicates that the imaging exam was proper but rather may result in a normal imaging exam (or only unrelated findings). That is, a certain number of normal results does not necessarily indicate that an imaging exam should not have been performed but rather are to be expected. However, if the proportion of normal imaging exams exceeds an expected level, this may indicate that the imaging exam is being overused. Examples of these and other possibilities will be discussed further below.

Because the comparison between the reason for exam code and the imaging exam report code is complex, the comparison may be used in several ways depending upon the clinical situation. In some cases, the comparison may use groups of imaging exams and may use a scoring system or percentages as thresholds to determine whether, within the group, the imaging exams were being requested appropriately, such as using the correct reasons for exam codes or the correct type of imaging exam for the clinical situation.

In a first example, a specific reason for exam code A and a specific type of imaging exam X may be compared to a specific imaging exam result code B. In this embodiment, the reason for exam code A and the imaging exam result code B may be different codes with a known positive relationship for exam X. A positive relationship means that, given the reason for exam code A, the selected imaging exam X is an appropriate type of imaging exam for the diagnosis indicated by the exam result code B. Nevertheless, not all patients with reason for exam code A, receiving imaging exam X, will end up having exam result code B. In a group of patients all having reason for exam code A and receiving imaging exam X, some will end up with an exam result code B while other patients will not, even though all cases the use of imaging exam X may have been appropriate for these patients. Therefore, on an individual basis, a patient having the reason for exam code A and the undergoing the imaging exam X may receive a variety of diagnoses, which may or may not include the exam result code B. This is to be expected and does not necessarily indicate a problem. For example, a patient may have not have received an exam result code B but rather may have received an exam result code C. Exam result code C may, just like exam result code B, be positively associated with reason for exam code A and imaging exam X, meaning that imaging exam X may be an appropriate way of diagnosing exam result code C in the context for a patient with a reason for exam code A. Other exam result codes D and E, for example, may also be positively associated with reason for exam code A and imaging exam X. These examples are shown in Table 1, below.

TABLE 1

| examples of appropriate use of an exam X | | |
|---|---|---|
| Reason for Exam | Exam | Possible Exam Report Diagnoses |
| A (headache with neurologic deficit) | X (MRI of brain) | B (aneurysm) C (mass) D (hemorrhage) E (infection) Normal |

In the first example discussed above, various embodiments may evaluate a group of patients having reason for exam code A for undergoing imaging exam X with regard to the exam result codes. For this group of patients, if reason for exam code A is selected correctly by the ordering physician and if imaging exam X is ordered appropriately for all patients in the group, a certain percentage p of the patients would be expected to have exam result code B. This percentage p is the ideal percentage and could be determined from statistical analysis of data from other large groups of similar patients, from literature reports, or other relevant sources, for example. Depending upon the actual reason for exam, imaging exam used, and exam result diagnosis, this number could be as low as one percent or less or as high as nearly 100 percent, though in many cases it may be a few percent, for example.

In some embodiments, this ideal percentage p could be used as a threshold value t. In other embodiments, the threshold value t could be determined based upon p and/or similar information. For example, the threshold value could be raised or lowered compared to p to account for normal statistical variation and/or differences between groups of individuals. For example, the threshold value t could be p plus (or minus) one standard deviation, or plus (or minus) two standard deviations. The actual threshold value t may be selected based upon how stringent of a comparison is desired, reflecting a tradeoff between detecting more problematic situations versus including more false positives in the comparison. This may in turn depend upon the expense of the particular imaging exam. For more expensive imaging exams, a threshold value which is at or very close to p may be preferred for detecting more actual errors and avoiding wasted cost even if it also results in the false detection of errors which then require time to eliminate as actual problems.

Various uses of a threshold value t that may be used in various embodiments may be considered using the example described above. For a group of patients having a radiologic imaging exam X with a reason for exam code A, the system may examine the frequency of an exam result code B in the group and compare it to the threshold value t. Since exam result code B is a proper result for an imaging exam X with a reason for exam code A, the system may determine that there was likely no problem with the imaging exams ordered for that group if the frequency of exam result code B was above the threshold value t. In contrast, if the frequency of exam result code B was below the threshold value t, this may indicate that there was a problem with the ordering of imaging exam X in this group of patients. For example, some of the patients in the group may not have been evaluated properly or may not have gone through all of the appropriate steps prior to receiving the imaging exam X, and as such some patients who should not have received imaging exam X received it nonetheless. As a result, a lower percentage of patients had exam result code B than would be expected if the appropriate steps had been followed. In this case, a frequency of exam result code B beneath the threshold t may indicate that the imaging exam was over utilized by an ordering provider or group of providers.

An example of a scenario in which overutilization may occur and may be detected by the system as described above is the use of an MRI for patients with headaches to detect a brain aneurysm. An MRI is useful and is an appropriate imaging exam for diagnosing causes of headaches such as aneurysms and masses within the brain. However, these types of conditions are uncommon, while the overall number of patients who suffer from headaches is very high. Therefore, it would be a poor use of resources to send all patients who suffer from headaches for MRIs of the brain. Rather, an appropriate evaluation may include steps such as a thorough exam and history to evaluate for neurologic deficits, various treatment attempts, and observation over time prior to ordering an MRI. Only in certain circumstances, depending upon the results of the evaluation and other steps, would an MRI of the brain be warranted. A physician who follows the appropriate steps when deciding whether to order an MRI of the brain for a patient with headaches is likely to have a frequency of finding brain aneurysms, for example, which is consistent with other physicians following the same appropriate steps. Thus, in terms of the examples described here, the reason for exam code A is the code for a headache, the imaging exam X is an MRI of the brain, and the exam result code B is the code for a brain aneurysm. The ideal percentage of cases in which a brain aneurysm is found p may be, as a hypothetical value, 2%. The threshold value t may then be set at 1% or possibly lower than 1%, such as 0.5%. For a physician following the appropriate steps prior to ordering the MRI, the frequency of patients having an exam result code B indicating an aneurysm may be expected to be at or above the threshold value t. The quality analysis system would thus detect a frequency at or above the threshold value t, indicating that there was likely no problem with errors in the ordering of imaging exam X for this physician. In contrast, a physician who does not follow the appropriate steps may have a lower frequency of patients having a brain aneurysm and this frequency may fall below the threshold value t. In such a case, the quality analysis system may detect a problem with possible errors in the ordering of exam X by this physician. Based on this comparison, the quality analysis system may alert a user to a potential problem, which the user may take as a cue for further investigation and possible future corrective action. Such corrective action, when taken by an insurer or hospital system, may include a denial of reimbursement or a decrease in reimbursement or a refusal to authorize an exam, for example.

In practice, when ICD-10 codes are used, there are many codes corresponding to a particular diagnosis such as brain aneurysm. As such, exam result code B would likely not be a single exam code but rather many exam codes which may be considered together. For example, there are many different locations at which aneurysms occur in the brain, and each location/artery may have its own distinct ICD-10 code, though some individual ICD-10 codes may represent multiple locations/arteries. That is, many ICD-10 codes may correspond to a single general diagnosis (e.g., brain aneurysm) and multiple specific diagnoses (e.g., posterior cerebral artery aneurysm, anterior cerebral artery aneurysm) may be represented by a single ICD-10 code. As such, while this description refers to exam result code B, for example, this is for simplicity of explanation and it should be understood that exam result code B may actually be a sing code or multiple codes which all cover various examples of a particular diagnosis, such as various locations of the same disease process.

In addition, a single reason for exam code for a particular radiologic imaging exam may be positively associated with multiple different imaging exam result codes. For example, reason for exam code A for imaging exam X may be positively associated with exam result codes B, C, D and E. The frequency of the exam results codes may be considered for each exam code result separately, as described above with regard to exam result code B. Alternatively, the frequency of occurrence of some of them or all of the positively associated exam result codes may be considered together and compared to a threshold t. As with a single exam result code, the frequency of a group of exam result codes may be compared to a threshold t, to determine whether the frequency is at or above the threshold or if it is below the threshold. For example, there are multiple conditions which may be diagnosed using an MRI of the brain in the clinical setting of headaches. As such, for a reason for exam code of headaches for an imaging exam MRI of the brain, positively associated exam result codes include, for example, aneurysms, intracranial masses, hemorrhages, infectious processes, previous injury due to hemorrhage, atrophy, autoimmune disorders, inflammatory disorders, and many more, each of which encompasses many distinct codes under the ICD-10 depending upon location and other features. The frequency of each of these codes may be used by the quality analysis system for comparison to the reason for exam codes separately, in groups according to a type of condition (e.g. all codes for aneurysms in the brain), or in groups including more than one condition or including all conditions.

In other embodiments, the quality analysis system may be used to analyze the frequency with which radiologic imaging exams are used to diagnose conditions for which the exam is not appropriate. In the example discussed above, this includes the use of imaging exam X for patients with reason for exam A with exam result codes Q, R, and S, where Q, R, and S are diagnoses that should not be diagnosed by imaging exam X and thus there is a negative association. There are many reasons why a particular imaging exam might be the wrong test to perform to diagnose a condition. For example, imaging exam X may be capable of providing diagnoses of Q and R, for example, but a different imaging exam Y might be better. For example, imaging exam Y might be more sensitive or specific, might provide more information, may be performed more quickly (such as in a life-threatening situation), or may be less expensive than exam X for exam result codes Q and R. Alternatively, exam X might be just as good or might even be better (more sensitive or specific or providing more information) than exam Y, but imaging exam Y might be less expensive, or more readily available, and still good enough for providing a diagnosis and therefore may be the better choice. For example, CT is much less expensive than MRI but is quicker and more readily available, and also can be more sensitive to diagnoses such as acute hemorrhage, so CT may be preferred in the setting of acute trauma. However, MRI (while more expensive), can detect acute stroke and brain masses better than CT, where these lesions can be nearly invisible on CT. Hence, whether in the acute or chronic setting, the correct modality (CT, MRI, etc.) depends on the symptom, indication, and most likely diagnosis suspected by the ordering clinician. In other examples, imaging exam X might be incapable of providing diagnoses corresponding to imaging exam result codes S, while imaging exam Y is capable of and is best for providing diagnoses corresponding to imaging exam result code S and T.

In the case of exam result codes Q and R discussed above, for which imaging exam X is capable of providing diagnoses but is not preferred in the setting of a reason for exam code A, the system can be used to detect such inappropriate use of imaging exam X. When the selection of the reason for exam as A and the selection of the imaging exam X are done appropriately, there should be very few or possibly no exams that result in imaging exam code Q, for example. That is, p may be very low or may be zero. Therefore, a threshold value t may again be used in this example to assess the imaging exam result code frequency in the context of reason for exam A and imaging exam X, with the threshold value t determined based upon data gathered from a set of appropriate imaging exam requests. In this case the threshold value t may be the limit, above which there may be a problem. As such, t may be set as equal to p or possibly greater than p to allow for statistical variation for example. The quality analysis system may compare the percent of exam result codes that are Q (out of all patients with the reason for exam code A and exam X) for a group of patients and compare it to t. If the percent for the group is greater than t, this may indicate a problem with potential ordering errors within the group. For example, fractures of the radius can generally be diagnosed with X-ray, though in a small number of cases a CT may be appropriate, such as in the setting of complex fractures requiring surgery. Various embodiments may determine the percent of CT scans of the forearm which were ordered for a reason for exam of forearm trauma which result in imaging exam results of radial fractures for a particular ordering physician or group of ordering physicians. If this percent is greater than a threshold, it may indicate that the ordering physician or physicians are over-utilizing the CT scan in this clinical setting. Alternatively, in various embodiments the system may one or more patients who underwent CTs of the forearm for forearm injuries and search their medical records to determine what percent had a previous X-ray of the forearm, such as by looking for previous exam orders or exam reports for each patient. This examples are shown in Table 2 below.

TABLE 2 examples of appropriate and inappropriate use of an exam X

| Reason for Exam | Exam | Possible Exam Report Diagnoses |
| --- | --- | --- |
| A (injury to forearm) | X (CT of forearm) | A (complex radial fracture) (appropriate use of exam X) Q (simple radial fracture) (inappropriate use of exam X) Normal |

In the case of exam result codes S discussed above, for which imaging exam X is not capable of providing a diagnosis, the system can be used to detect such inappropriate use of imaging exam X. When the coding of the reason for exam as A and the selection of the imaging exam X are done appropriately, there should be no near future exam Y that results in imaging exam code S, for example. An example of this is shoulder pain due to a labral tear, as shown in Table 3 below. A first exam X, MRI of the shoulder, was performed for shoulder pain. However, the MRI of the shoulder was normal. In some cases, the shoulder MRI might be repeated, and still return a normal result. In a subsequent exam Y, an arthrogram of the shoulder was performed and a diagnosis of a labral tear was identified. The original use of the MRI of the shoulder was inappropriate because it was incapable of detecting a labral tear. Such inappropriate exams, which are performed for diagnoses which they are not capable of identifying, can only be identified by looking at subsequent information in the patient's medical record such as future exam reports or post-exam encounter diagnoses. Various embodiments therefore may identify the inappropriate use of an exam by comparing a reason for exam and/or exam type to later diagnoses on in a subsequent exam report (for a different type of exam) or post-exam encounter.

TABLE 3 examples of an inappropriate and subsequent appropriate exams

| Reason for Exam | Exam | Exam Report Diagnoses |
| --- | --- | --- |
| A (shoulder pain) | X (MRI of shoulder) | Normal |
| A (shoulder pain) | Subsequent exam Y (MR Arthrogram of shoulder) | S (labral tear) |

The actual comparisons and threshold values used will vary depending upon the type of examination, the reason for exam code, the post-exam encounter code, etc. However, it may be useful to focus on types of radiologic imaging exams and reasons for exam codes which are known to be problematic and/or which generate significant costs to automatically identify potential problems.

An example of one possible structure of a system to implement the methods described herein is shown in FIG. 1. The system includes databases and memory as well as programming instructions or scripts for performing the steps of the methods described herein. These databases and programming may be stored in and implemented by the memory and processor of multiple servers as shown in FIG. 1 or in other configurations and may include tangible or non-transitory computer readable or computer accessible media, for example. Some or all of the databases and programming may be located on one or more remote servers, such as servers in the cloud, to be accessed through the internet or by other electronic communication, or on the servers of a hospital or other medical service provider's computer system, or on the servers of a quality analysis system services provides, or on the servers of a coding service provider's computer network, in combination or separately. As such, the quality analysis system described herein (and optionally a coding services provider system) may be incorporated into a computer system of a health care provider network such as a hospital and clinic organization and may enable automation. Alternatively, the quality analysis system may be incorporated into a computer system of a medical coding entity. Alternatively, the quality analysis system may be entirely separate from either the computer system of the health care provider or the medical coding entity but in electronic communication with the computer systems of the health care organization and the medical coding entity. Regardless of its physical implementation, whether physically separated or partially or entirely together, the components of the quality analysis systems discussed herein may be electronically linked to allow communication between them. Furthermore, although each of these is shown as a single servers, each of these could include multiple servers with the elements as shown optionally distributed amongst them. In addition, although shown as separate, one or more of these servers or the components stored on or performed by these servers could be integrated together into the same server or server system, and the components could be located together on the same server or separately.

An example of a system according to various embodiments is shown in FIG. 1, which includes a medical record analysis system server 10, a medical services provider server 40, a coding service provider 30, and a quality analysis system server 80, among other things. The medical record analysis system server 10 may be an exam report analysis system server, an exam order analysis system server, and/or an encounter analysis system server, depending upon which functions are needed by the system, which may be included together on one server or separately on a plurality of servers. Furthermore, in the example shown in FIG. 1, the medical services provider server 40 is separate from the medical record analysis system server 10, the coding services provider server 30, and the quality analysis system sever 80, though they are in electronic communication with each other. Although each of these is shown as a single server, each of these could include multiple servers with the elements as shown optionally distributed amongst them. Furthermore, although shown as separate, one or more of these servers or the components stored on or performed by these servers could be integrated together into the same server or server system, and the components could be located together on the same server or separately.

In the example shown in FIG. 1, the quality analysis system operates on quality analysis server 80 which includes a processor 82 on which the quality analysis system programming 84 operates. It further includes a memory 86 on which the comparison database is stored. The memory 86 may also include other databases such as a database of generated data 86.

The coding service provider server 30 similarly includes a processor 34 on which the coding programming 32 operates for user review of reports and entry of codes and memory 36 on which the coded report data 38 is stored. The medical service provider server 40 includes a processor 42 on which the dictation programming 44 may operate as well as memory on which medical records 48 may be stored including distinct medical reports 40 and exam orders 52. In operation, a service provider such as a physician (including someone acting on behalf of the physician) enters an order or report into the medical service provider server 40 through a user interface 60 such as a microphone of a computer or voice recording device or dictation system for voice dictation, or a keyboard for typed orders and reports, for example. The user interface 60 may directly interact with the medical service provider server 40 or through a provider's computer or by other means.

The medical services provider server 40 as shown includes dictation processing programming to automatically transcribe the verbal dictation of the report (which may be an imaging exam report or a post exam encounter report, for example) into a text report 50. However, such functionality may not be included. In some embodiments, transcription may not be necessary or may be performed separately, outside of the medical service provider server 40, by a transcription service provider, for example, and the text report 50 may be separately uploaded into the medical records 48. A user, such as a coder, researcher, or supervisor, may interact with the coding services provider server 30 and/or with the report analysis system server 10 through a second user interface 70 such as a keyboard 74 and screen 72 of a computer 76.

The medical record analysis system (including a report analysis system, exam order analysis system, and/or encounter analysis system) operates on medical record analysis server 10 which includes a processor 12 on which the medical record analysis programming 14 operates. It further includes memory 16 on which the diagnostic database 18 is stored. The memory 16 also includes other databases including the database of words of exclusion 22, the database of words of substitution 24, and the database or words of negation 26. These databases 18, 22, 24, 26 and any other databases may be stored as separate databases as indicated or one or more or all may be stored together in a single database including database tables, for example. Generated data 28 produced by the report analysis system may also be stored in the memory 16.

The embodiment shown in FIG. 1 includes a medical record analysis system using medical record analysis system server 10, though in alternative embodiments the quality assurance system may not include a medical record analysis system. Rather, coding of imaging exam results, reasons for exam, and/or post-exam encounter diagnoses may be performed using other methods such as traditional manual review of the imaging reports by users interacting with the coding service provider server, or coding may not be required as the original entries (such as for the reason for exam in the order and the post exam encounter diagnoses in the post exam encounter report) may be entered by the physician in the form of an alphanumeric code. In such embodiments, the quality assurance system may resemble the system shown in FIG. 1 with the exclusion of the report analysis system server 10.

In still other embodiments, the coding service provider server 30 may provide information regarding coded reasons for exam, exam reports and/or encounter diagnoses to the medical service provider server 40 and this information may be stored in the memory 46 of the medical service provider server 40. In such a case, the quality analysis system server 80 may not communicate directly with the coding service provider server 30 as shown in FIG. 1. Rather, the quality analysis system server 80 may interact only with the medical service provider server 40 to obtain the reason for exam codes, exams report codes, and post exam encounter codes, as well as other relevant information such as the identity of the ordering physician, etc. In still other embodiments, information regarding the reason for exam codes, the exam report codes, the post exam encounter codes and/or other relevant data may be available through the coding service provider server 30 and may be stored in memory 36. In such embodiments, the quality analysis system server 80 may interact only with the coding service provider server 30 to obtain the necessary data and may not interact with the medical service provider server 40. In other embodiments, still other arrangements are possible, such as systems in which some or all of the data used by the quality analysis system 80 is stored separately and is available to the quality analysis system 80 separately from any of the servers shown.

Figure 2:
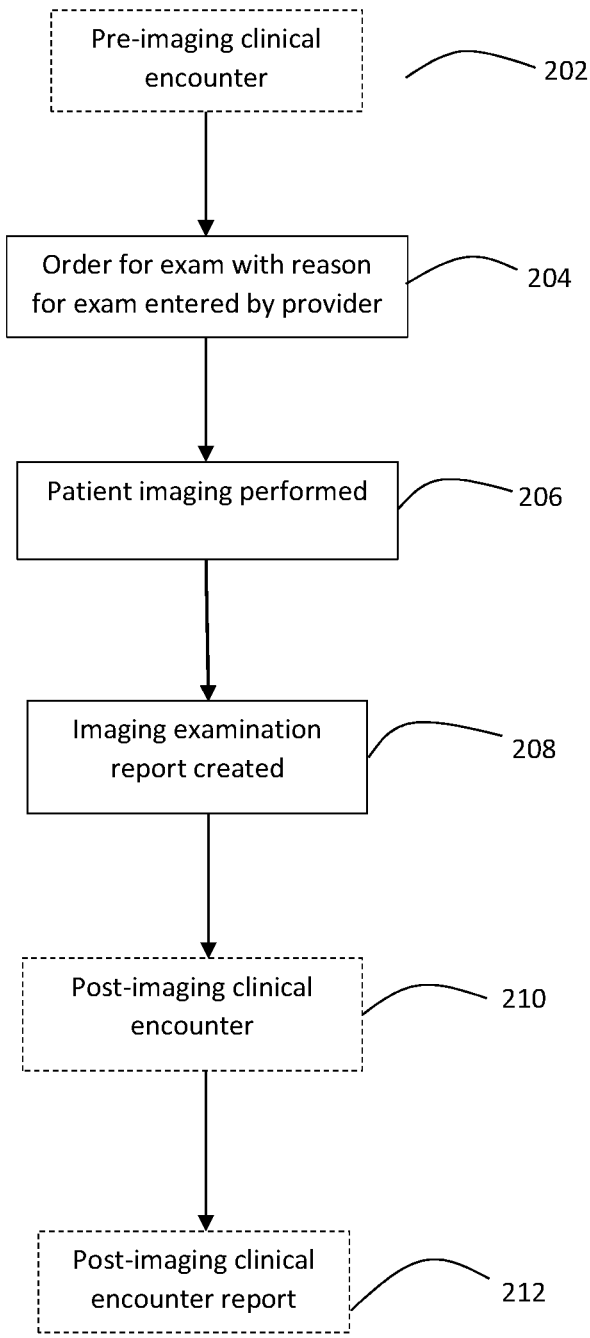
FIG. 2 is an example of a process for generating exam orders, exam reports, and post exam encounter diagnoses for a patient.

FIG. 2 is a depiction of steps of generating exam orders, exam reports, and post exam clinical diagnoses, according to typical steps for an example patient. In step 202, a patient has an encounter with a medical professional such as a physician. This encounter may be, for example, an outpatient appointment in the medical professional's office, an inpatient examination by the medical professional, or a telephone call with the medical professional, for example. Based upon this encounter, the medical professional may determine that the patient should have a radiologic imaging exam. In some cases, the patient may not have a pre-imaging clinical encounter but rather the medical professional may determine that the patient needs a radiologic imaging exam based upon some other encounter or information, such as the results of a previous imaging exam, laboratory results, or a different reason.

In step 204, the ordering physician (which includes someone acting on behalf of the ordering physician and who may not be a physician but rather a physician's assistant, for example) orders the radiologic imaging exam, such as by inputting an order into the medical service provider system 40 such as an electronic heath record (EHR) or radiology information system (RIS). This order includes one or more reasons for exam which may be in the form of plain text or in the form of a reason for exam code.

In step 206, the radiologic imaging exam ordered in step 204 is performed on the patient. A radiologist then reviews the images produced by the radiologic imaging exam. In step 208, the radiologist then creates an imaging examination report including a verbal description of the normal and/or abnormal conditions identified by the radiologist in the radiologic imaging exam.

In some situations, the imaging exam may be the last step as no further medical encounters or interventions may be needed. In other situations, the patient may have a post-imaging exam clinical encounter in step 210. As with the pre-imaging clinical encounter, the post-imaging clinical encounter may be an outpatient appointment in the medical professional's office, an inpatient examination by the medical professional, or a telephone call with the medical professional, for example.

In step 212, a medical professional creates a post-imaging encounter report including one or more post imaging diagnoses. The post-imaging encounter report may be entered electronically into the medical service provider system 40 in electronic form. Some or all of these post imaging diagnoses may be the same as the diagnoses in the reason for exam and/or in the exam report or may be different. These post imaging diagnosis may be entered in plain text format and/or as an alphanumeric code.

Figure 3:
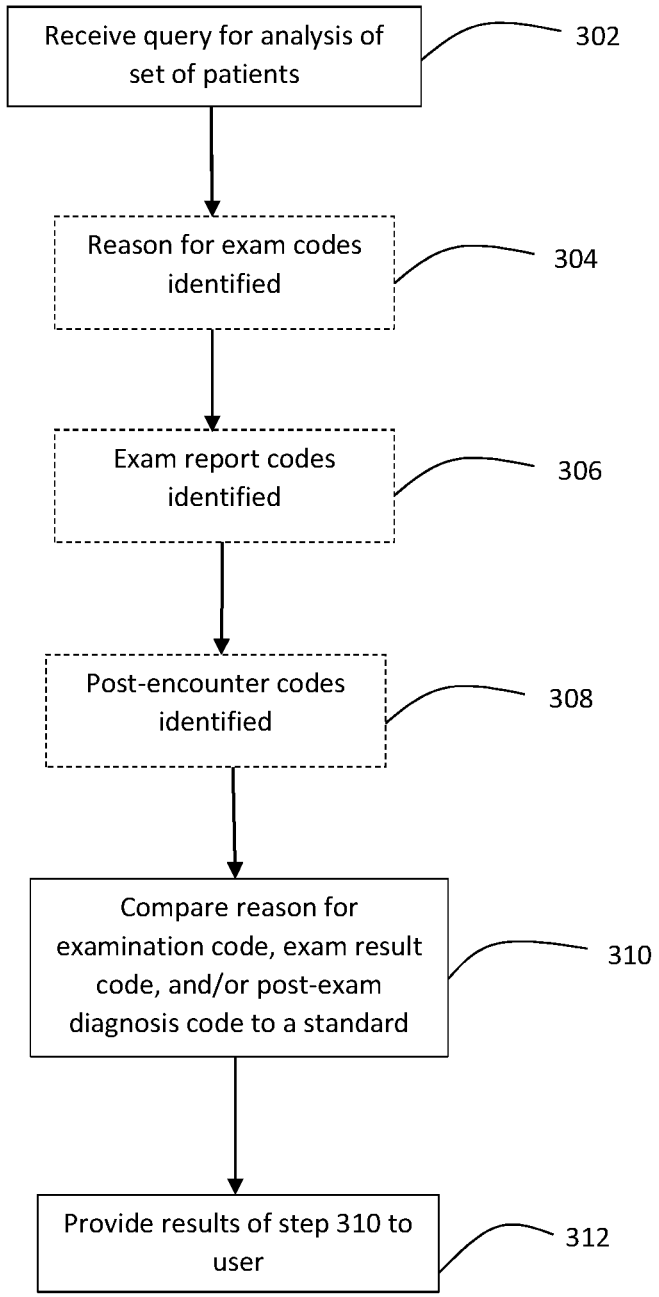
FIG. 3 is a process for quality analysis of a group of radiologic imaging exam orders.

A process for quality analysis of the ordering of radiological imaging exams by a quality analysis system is shown in FIG. 3. The process begins when either a user submits a query into the quality analysis stem or the system is set to automatically perform a query at a particular time. The query may be a request for the analysis of data for a set of patients who received radiologic imaging exams. The query may specify parameters including one or more of a time period during which the exam was order or performed, the ordering physician(s) or group of physicians or institution, the type of exam, the reason for exam, the reason for exam code, the exam result code, the post exam clinical encounter code. For example, the set of patients may be identified as having one or more characteristics in common such as the following: having received a particular radiological imaging exam; having had a particular reason for exam code for a particular radiological imaging exam; and/or receiving a particular imaging exam result code. Other characteristics which may be used to define the set of patients may be one or more of: having received the radiological imaging exam during a particular time frame, from a particular service provider (or from an entity or individual in a group of providers), the identity and/or institution of the ordering physician, etc. The set of patients may be broad or narrow, and in some embodiments the characteristics of the set may be defined by the user and input into the quality analysis system as a request for a comparison. In step 302, the quality analysis system receives the query, which may be automatic or input by a user.

In steps 304, 306, and 308 the system identifies the request for exam codes, the exam report codes, and the post-encounter diagnoses codes respectively for the set of patients. However, depending upon the nature of the query, the system may only need to identify one or two of these codes for the set of patients, though for some queries it may need to identify all three. These codes may be culled from the medical records 48 of the medical service provider server or from another source such as the coding service provider server or from with the memory 86 of the quality analysis system server 80 itself, depending upon the structure of the system. The results may be requested according to a query from the quality analysis system server 80 which may be input by a user or may occur automatically, for example.

In step 302 the system may identify the reason for exam codes directly from the exam orders if the order were entered using codes and may be found in the medical service provider system, for example. However, if the exam orders were entered in a free text form, the medical record analysis system may first need to automatically convert the reasons for exam in free text form into reasons for exam codes which can be used by the quality analysis system.

In step 306, the exam report codes might exist and be available from the medical service provider system and/or the coding service provider system if the exam reports have already been processed by coders. In some cases, the medical record analysis system may first need to automatically convert the exam report into exam report codes which can be used by the quality analysis system.

Similarly in step 308, the post-imaging clinical encounter diagnosis codes may exist and be available in the medical service provider system and/or on the coding service provider system if the post-imaging encounter diagnoses were entered by the medical provider in the form of a code initially or if the post-imaging clinical encounter report has already been processed by coders. In some cases, the medical record analysis system may first need to automatically convert the post-imaging clinical encounter diagnoses into post-imaging encounter codes which can be used by the quality analysis system.

Once the set of patient imaging exams has been defined and the data including the codes (request for exam, exam result, and/or post-imaging encounter diagnosis) for the patients in that set received by the quality analysis system, the reason for exam code, the imaging exam result codes and/or the post-imaging encounter are compared to a standard or a set of standards in step 310. These standards may be a threshold value as described above, a score based on binary values or other scoring system, or other statistical evaluations or calculations to identify correct or appropriate versus incorrect or inappropriate ordering and use of medical imaging.

Alternatively, the system may score the reason for exam code, the type of exam, the exam result code, and/or the post exam encounter diagnosis code, depending upon the type of analysis being performed. The proportions or frequencies with which specific exam diagnosis codes were the result of various reason for exam codes and post exam encounter diagnoses may be monitored and updated continuously. Various mathematical calculations can be used to score whether the combination of one or more of these diagnosis codes was appropriate or not for a particular patient relative to the exam result code, for example, and these scores may be combined for the group included in the query. In some embodiments, the scoring system may be binary, with a score of 1, for example, given if the combination is appropriate and a score of 0 if the combination is inappropriate.

An example of the application of a binary scoring system may be the use of a CT of the head for a reason for exam of a worst headache of the patient's life. In such a case, the CT of the head is appropriate to check for a subarachnoid hemorrhage. In this scenario, if the exam result finds a subarachnoid hemorrhage, the comparison of the reason for exam (worst headache of life) to the exam result (subarachnoid hemorrhage) will be scored as 1. However, if the exam result finds no subarachnoid hemorrhage, the comparison will be scored as 0. The scores of a group of patients having a worst headache of their lives and a head CT may be each scored in this way and their total score or their average score compared to a threshold. For example, if an average score is used, the average would be between 0 and 1, with a score closer to 1 indicating more diagnoses of subarachnoid hemorrhage and therefore more likely appropriate use of the exam.

In the example described above, the group of patients could include only those who received a head CT or it could include other types of exams as well. For example, some patients with a reason for exam of the worst headache of the patient's life may undergo an MRI of the head, which is still capable of detecting subarachnoid hemorrhages but may be insensitive to small amounts of acute subarachnoid hemorrhage. If the same binary scoring system discussed above is used, in some cases the comparison will result in a score of 1 (reason for exam was worst headache of the patient's life and the exam result was a subarachnoid hemorrhage) while others will have a score of 0. However, because it is not as sensitive of an exam, the total or average score for a group of patients including (or limited to) those who received an MRI will be lower that a group that only receive the preferred exam, a CT of the head. This lower score may be below a threshold, which may indicate correctly that there was a problem with the utilization of the radiology exams in this group.

The results of the comparison in step 310 may be provided to a user in step 312. This user may be the same as the user who entered the query or a different user. The results may be provided as simple mathematical results of step 310, or they may be further processed to make them more useful to a user, such as by indicating whether the data used in the analysis complied with the standard, such as whether it was above or below the threshold value or score, whether or not this result indicates a potential problem, or whether or not this result is divergent from expected proportions or frequencies of trends in associations of diagnoses. In some embodiments, the results may provide the user with suggestions about what the problem could be.

In the example described above, the comparison between the reason for exam, exam result, and/or post exam encounter diagnosis includes a group of patients having one or more features and/or aspects of the exam in common. However, comparisons and evaluations of the reason for exam, exam result and/or post exam encounter diagnoses may also be made for individual patients to automatically identify potential problems with the ordering of radiological exams. For example, a user could query the system for all patients within a group (such as patients of a particular physician or physicians' group or at a particular institution) who underwent a particular type of exam at least a certain number of times (which could be set by the user) and had normal results (or no relevant pathological results) every time. This may indicate that the exam is being overused on this patient, since no useful information is being gained. For example, the system may identify patients who have had MRIs of the brain for a reason for exam of headache and analyze the exam results. If there is no relevant exam result related to headache (such as an aneurysm, mass, etc.), and yet the MRI is performed repeatedly, such as three times or more, this may indicate a problem with the ordering of the exam. In another example, the system could identify patients in an outpatient, non-acute setting who underwent an advanced imagining study such as CT or MRI with a reason for exam of a particular injury such as a knee injury. Among these patients, the system may further look at the patients' medical records to determine whether or not the patients first underwent a plain film X-ray, which is the appropriate procedure because the plan film X-ray is a cheaper, easier, and, as compared to a CT, exposes the patient to less ionizing radiation. The system may identify those individuals who did not first have a plain film X-ray as potentially indicating a problem with the ordering of the exam. In a third example, the system could identify patients who underwent MRI's of the lumber spine for a reason for exam of low back pain. Among those patients, the system may look for additional criteria justifying the MRI such as associated diagnosis indicating a risk of spinal cord injury such as fecal incontinence, lower extremity weakness, or numbness of the groin or rectal area, and/or length of time since the injury or onset of pain. For those individuals who do not have additional criteria in their medical records, the system may identify and indicate a potential problem with the ordering of the exam. In cases such as these, the system may automatically identify such cases and present them to the user.

One example of a medical record analysis system which may be used in various embodiments as the source of reason for exam codes, exam report codes, and/or post-exam clinical encounter codes, such as when these were original entered in free text form, for use in the quality analysis system is described below. The medical record analysis system may be used to generate diagnoses in the form of alphanumeric codes from the request for examination section of the radiologic imaging exam order, from the radiologic imaging exam report, and/or from the post-imaging clinical encounter report. The alphanumeric diagnoses codes obtained using the medical record analysis system may be used as the request for examination codes, exam report codes and/or post imaging encounter codes by the quality analysis system. However, as mentioned above, the exam report codes may alternatively be provided by the medical provider entering the order, the exam report or the encounter report of by individual reviewers such as coders or other types of report analysis systems or methods which likewise provide alphanumeric diagnoses codes which may be used as the request for exam, exam report, or post imaging encounter codes by the quality analysis system described herein. Some or all of the alphanumeric codes, obtained either automatically or by an individual, may be stored in digital memory, such as in a database for each patient, for later use by the quality analysis system such as when performing user queries or in response to pre-programmed queries. Alternatively, the quality analysis system may obtain some or all of the alphanumeric codes from patients' electronic records and/or from analysis of patients' records, such as records within the electronic medical record, when it received a query.

In the example medical record analysis system described below, the medical record analysis system may include various servers including processors and databases as shown in FIG. 1. For example, it may include a database of standardized sets of diagnosis. The particular of standardized set of diagnoses (or other information) used by the medical record analysis system will depend upon the desired output and will be included in and employed by the medical record analysis system in the form of a diagnosis database (or other database of information). For example, if the desired output of the medical record analysis system is a set of ICD-9 diagnosis codes (numerical codes), the medical record analysis system may include and may employ a database of ICD-9 codes and corresponding diagnosis terms (text descriptions). Similarly, if the desired output of the medical record analysis system is a set of ICD-10 terms, it may include an employ a database of ICD-10 diagnosis codes and corresponding diagnosis terms. Such a database may be in the form of a table or other useful form. In some embodiments, the medical record analysis system may include more than one database, such as two or three or more databases. In such embodiments, the medical record analysis system may automatically use the more than one database in performing an analysis of reports. Alternatively, the user of the medical record analysis system may select a single database or multiple databases to be employed by the medical record analysis system, or the user may select the type of desired output (the type of codified data) and the medical record analysis system may automatically use the corresponding database when analyzing a report, to obtain the desired type of output.

The databases used in various embodiments may be created using standardized sets of diagnoses, procedures, and other information and the associated alphanumeric codes which may be commercially available as databases or alternatively as tables or lists that may be converted into databases for use by the medical record analysis system. These databases may be included in the medical record analysis system as they are, without modification of the language as it exists in the standardized format, or the language may be modified for use in the medical record analysis systems in order to improve the process of matching the database to the text of the request for exam, exam report or encounter report. The medical record analysis system may include the database with the language in original, unmodified form, as well as the language in modified form. Alternatively, the medical record analysis system may consist of two databases, one with the language in the original, unmodified form, and the other with the language in modified form, with each database including the associated alphanumeric code for each diagnosis (or procedure or other information).

The medical record analysis system may also include other databases for use in analysis of the exam order, exam reports and post exam encounter reports. Such databases may be tables of words or phrases and may be created manually for use in the medical record analysis system. For example, one database which may be included in the medical record analysis system may be a table of words to be excluded from the report. Words to be excluded may be words which function as a part of natural language but which do not convey information relevant to the diagnosis, procedure, or other information. Examples of such words include "and," "the," "any," "at," "by," "are," "has," "from," "in," and "into," some or all of which may be excluded, and other additional words may likewise be excluded, depending upon the database. When these excluded words are included in the diagnosis database and/or in the report, the medical record analysis system may ignore them or delete them and not consider them in any subsequent analysis or comparison.

Another example of a database which may be included in the medical record analysis system is a database of words for substitution. Such a database may be manually created and may be a table of words with equivalent meaning, for example. The substitution database may be used by the medical record analysis system in order to improve the matching of the language in the reports to the language in the diagnosis database (or other database). This is particularly important since there are many synonymous words and abbreviations, even within the medical world, and different individuals, particularly individuals of different medical specialties, may draw upon different lexicons when creating their reports. This variability of language can make automatic analysis of reports difficult. For example, if the diagnosis database uses a particular word for a diagnosis, but a report uses a different word having the same meaning, when the diagnosis database is compared to the report, the automated medical record analysis system might not recognize them as being the same. However, if the equivalence of the meaning of the words is recognized by the automated medical record analysis system, such as through the use of a database of words for substitution, then the automated medical record analysis system can identify the diagnosis in the report as being the same as the diagnosis in the database. For example, the medical record analysis system may analyze the reason for exam, exam report and/or encounter report for words included in the substitution database and substitute such words for words included in the diagnosis database before comparing the report to the diagnosis database to the report. In embodiments in which the medical record analysis system employs more than one diagnosis database (or other information database), the medical record analysis system may have a corresponding database of words of substitution for use with each diagnosis database, since the words used in each database might vary and might therefore require a different set of words in the words of substitution database. In some embodiments, the substitution database may include abbreviations and the corresponding medical terms, such as ACA and anterior cerebral artery, MCA and middle cerebral artery, etc.

The variability of language used by clinicians when creating an exam order, exam report or encounter report can make it difficult for other clinicians, when reading the documents, to recognize important findings which may require further action on the part of the reading clinician. This is particularly true for the radiologic imaging exam reports. For example, certain findings may indicate that the clinician should order additional studies. In the radiology field, such findings may be referred to as actionable impressions, and it is important for the clinician reading the report to recognize them. However, since the language in the imaging exam report may be different from a standard language (such as a standard diagnosis in an ICD system) the clinician may not recognize the need for further action, such as the actionable impression, and may fail to provide appropriate care. The medical record analysis systems described herein, through the use of the substitution database as well as the other aspects of the system, may present the imaging exam results in a standardized and more recognizable and understandable way so that findings which require further action can be more easily recognized by the clinician for a higher level of care.

Reasons for exam in imaging exam orders, imaging exam reports, and post imaging encounter reports may include not only diagnoses of abnormal conditions but also observations that certain diagnosis and conditions are not present. This is particularly true for imaging exam reports and is likely, though not limited to, when a procedure is performed in order to determine whether a particular condition is present or to rule it out. In some circumstances, such a "pertinent negative" presence of findings may be critical for the clinician to note in a report, for example, as the presence or lack of a condition (e.g. hemorrhage) may dictate a patients care pathway, such as admission to the hospital or intensive care unit, or surgery. The medical record analysis system must be able to automatically determine whether the language of the report indicates the presence of a diagnosis or the absence of a diagnosis. Therefore, in some embodiments the medical record analysis system may include an additional database which is database of words of negation. This database may be a table of words, for example, indicating a negative finding in a report, meaning that the associated condition is not present. For example, a report of a chest X-ray might include the words "no evidence of pleural effusion." The medical record analysis system may apply the negation database when analyzing the report to identify any words of negation and to determine whether the report indicates that a condition or finding is present or not present. Examples of words which may be included in the negation database include "no," "not," and "absent." Other words of negation, which are atypical in that they indicate a normal condition but which may be misinterpreted by an automated system, may also be included. For example, the word "patent" with regard to vessels indicates that they are not stenotic or occluded. Such a word may be included in the database of words of negation as it indicates that a pathological condition is not present. Alternatively, such words may be included in the substitution database. For example, the word "patent" may be substituted for a words including those from the standard database, such as "no stenosis occlusion," in which case the word "no" would be detected by the database of words of negation.

In addition to one or more diagnoses databases (or other database) and databases used to refine the language to improve the analysis, the medical record analysis system also includes programming instructions or scripts for performing the steps of the methods described herein. These databases and programming may be stored in and implemented by the memory and processor of user's computer or may be stored on one or more servers outside of the user's computer on tangible or non-transitory computer readable or computer accessible media, for example. The databases and programming may be located on a remote server, such as a server in the cloud, to be accessed through the internet or by other electronic communication, or on the servers of a hospital or other medical service provider's computer system, or on the servers of a coding service provider's computer network (which may itself be a part of the hospital or medical service provider computer network). As such, the medical record analysis system described herein may be incorporated into a computer system of a health care provider network such as a hospital and clinic organization. Alternatively, the medical record analysis system may be incorporated into a computer system of a medical coding entity. Alternatively, the medical record analysis system may be entirely separate from either the computer system of the health care provider or the medical coding entity but in electronic communication with the computer systems of the health care organization and the medical coding entity. Regardless of its physical implementation, whether physically separated or partially or entirely together, the components of the medical record analysis systems discussed herein may be electronically linked to allow communication between them.

In the example shown in FIG. 1, the medical record analysis system operates on medical record analysis server 10 which includes a processor 12 on which the report analysis programming 14 operates. It further includes memory 16 on which the diagnostic database 18 is stored. The memory 16 also includes other databases including the database of words of exclusion 22, the database of words of substitution 24, and the database or words of negation 26. These databases 18, 22, 24, 26 and any other databases may be stored as separate databases as indicated or one or more or all may be stored together in a single database including database tables, for example. Generated data 28 produced by the medical record analysis system may also be stored in the memory 16. The coding service provider server 30 similarly includes a processor 34 on which the coding programming 32 operates for user review of reports and entry of codes and memory 36 on which the coded report data 38 is stored. The medical service provider server 30 includes a processor 32 on which the dictation programming 34 may operate as well as memory on which medical records 38 may be stored including distinct medical reports 40. In operation, a service provider such as a physician enters a report into the medical service provider server 30 through a user interface 50 such as a microphone of a computer or voice recording device or dictation system for voice dictation, or a keyboard for typed reports, for example. The user interface 50 may directly interact with the medical service provider server 30 or through a provider's computer or by other means. The medical services provider server 40 as shown includes dictation processing programming to automatically transcribe the verbal dictation of the report into a text report 50. However, such functionality may not be included and the transcription may be performed separately, outside of the medical service provider server 40, by a transcription service provider, for example, and the text report 50 may be separately uploaded into the medical records 48. A user, such as a coder, researcher, or supervisor, may interact with the coding services provider server 30 and/or with the medical record analysis system server 10 through a second user interface 52 such as a keyboard 74 and screen 72 of a computer 76.

Figure 4:
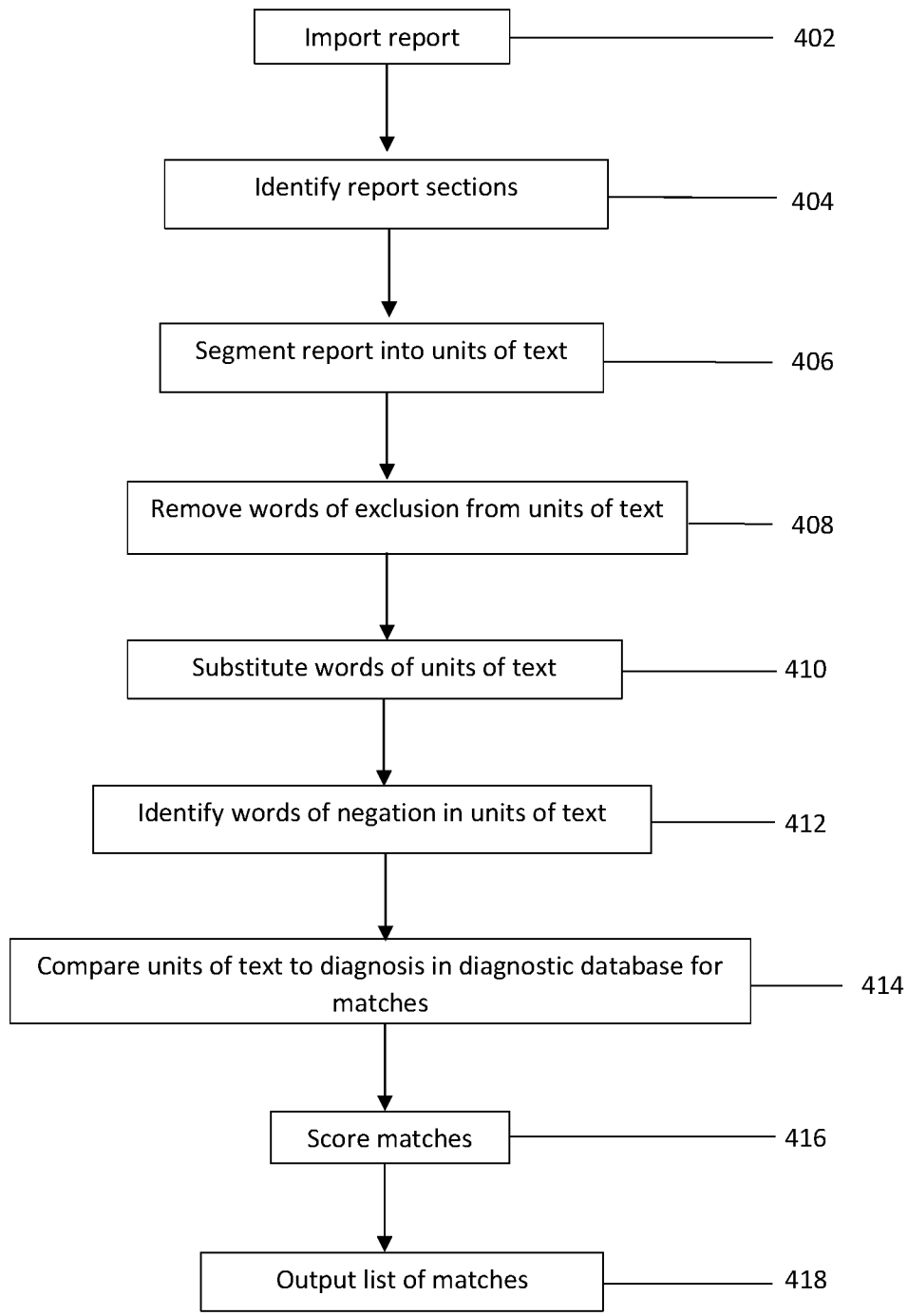
FIG. 4 is a flow chart of a method of analyzing a medical record according to an example of a report analysis system.

A user may direct the medical record analysis system to automatically analyze an exam report 50, which may occur through a series of steps such as those shown in FIG. 4. The steps shown in FIG. 4 are examples and while they may be performed in the sequence as shown, they may alternatively be performed in a different sequence and/or some steps may be performed concurrently. In addition, some steps may be omitted in some cases or additional steps may be added. Furthermore, while this example relates to the analysis of an exam report, the same steps may likewise be used for the analysis of an exam order or a post-exam encounter report.

A user may begin a medical record analysis of a radiological imaging exam order, report, or post-exam encounter report by directing the medical record analysis system to import a diagnosis database (or other database) as well as supplemental databases. In some embodiments, this process may occur automatically as part of initiating the programs of the medical record analysis system, while in other embodiments the user may specifically direct the medical record analysis system to import the databases. The supplemental databases may be automatically imported along with the diagnostic database without specific instruction from the user. Furthermore, in some embodiments, it may not be necessary to import these databases as they may already be stored within the medical record analysis system. Finally, in some embodiments the medical record analysis system may include various diagnostic databases and/or other databases of code associated text and the user may select which diagnostic database(s) and/or other database(s) will be used and therefore which database(s) will be imported and/or accessed by the medical record analysis system.

In step 402 the user may select an exam report 50 to be imported into the medical record analysis system. If databases are selected as described above, step 402 may be performed before or after the selection the databases. The exam report 50 that is imported may be in free text form, having been either typed directly or transcribed from a voice dictation. The medical record analysis system may import the exam report 50 from the medical records 48 which may be a part of an electronic health record system. Alternatively, when the medical record analysis system is used as part of a quality analysis of a set of imaging exam orders as described above, exam reports and/or post exam encounter reports, individual reports may not be selected by a user but rather the order(s) and report(s) may be automatically selected by the system according to the query.

After the exam report 50 is imported, the medical record analysis system may automatically perform a series of steps as described below, the order of which may vary from that shown. In step 404, the medical record analysis system may analyze the exam report 50 to identify different sections and extract relevant text from those sections. For example, for a radiology exam report, the medical record analysis system may look for and identify one or more or all of the standard sections including Title, Indication, Procedure, Findings and Discussion, and Impression. In some embodiments, the medical record analysis system only identifies the Impression section to increase specificity of identifying relevant diagnoses. In radiology imaging exam orders, the medical record analysis system may look for and identify one or more standard sections including the Reason For Exam or other discrete data elements of the order, such as free-text comments or multiple-choice order instructions, such as may be labeled "Comments" or "Order Instructions", or other similar and specific data elements relevant to that particular type of imaging order or computerized physician order entry system. In post exam encounter reports, the medical record analysis system may look for and identify one or more standard sections including order elements for imaging or other orders as previously described; clinical, imaging, or procedure examination notes in free-text, semi-structured, or structured forms; or other free-text or discrete data elements linked to encounters as part of the EHR. Sections of an order or report may be identified by their use of standard text as sections headings, and the medical record analysis system may scan for the standard text of the section headings to identify the sections. For example, the medical record analysis system may scan the exam report 50 for the word "Impression" to identify the impression section of an imaging report, or for the words "Assessment," "Plan," or "Conclusion" of a clinical examination report, to identify the conclusive elements of a clinical examination. The medical record analysis system may further look for and identify other information, apart from the standard sections, such as the name of the person creating the order or the report (such as the ordering physician or the reading radiologist). In some embodiments, the exam report 50 may segmented into sections at the time it is generated, such as into separate databases, depending upon how the exam report 50 is created. For example, the exam report 50 may be associated with the name of the individual who generated the exam report 50, such as the reading radiologist, and may be stored separately in the medical service provider server 40. In such embodiments, the medical record analysis system may obtain this information directly from the separate database in which it is stored. For example, the medical record analysis system may obtain the name of the reading radiologist directly from the medical service provider server 40 in which it is stored separately, in the same manner in which it accesses the report 40.

In some cases, the sections of the exam report 50 can include large amounts of text. Therefore, after identifying the sections of the exam report (or exam order or post exam encounter report), the medical record analysis system may take the text of one or more sections and segment it into smaller units of text in step 406. These units of text may be sentences which may be identified by the medical record analysis system by the presence of numbered points, periods, spaces, and/or other properties of sentence structure that may indicate the presence of separate sentences while differentiating such text from abbreviations, for example. In some embodiments, the units of text may be phrases which may be a whole sentence or maybe smaller than a sentence, depending upon the structure of the sentence. That is, some sentences may include a single phrase while others may include two or more phrases and the medical record analysis system may divide the section into units of text including whole and partial sentences. This may be done, for example, by identifying periods as well as other features such as commas and natural language conjunctive phrases to segments the text into units including sentences and to further segment the sentences into smaller units in some cases.

The medical record analysis system may further process the units of text in order to achieve more accurate final results. In step 408, the medical record analysis system may scan the units of text for words present in the words of exclusion database 22 to remove certain words from the units of text. In step 410, the medical record analysis system may scan the units of text for words present in the words of substitution database 24 and may substitute the words of the report with equivalent words used in the diagnosis database. In addition, in step 412, the medical record analysis system may scan the units of text for words present in the words of negation database 26 to identify words indicating negative findings. The final result of these steps may be a modified unit of text (though in some cases no actual modification may occur).

The modified units of text may then be compared to the diagnosis database in step 414. Each modified unit of text may be compared, one word at a time, to the words of each diagnosis in the database. When one or more words in the modified unit of text match one or more words in the diagnosis, the medical record analysis system identifies the diagnosis as a match for the unit of text.

In some cases, the goal of the comparison process in step 414 is to identify diagnoses (or reason for exam) from the diagnoses database that are most likely to be correct, that is, the same as the diagnosis identified in the unit of text of the report 50. However, the comparison process of step 114 can produce a large number of matches for each unit of text, depending upon the particular words used in the report 50. In addition, some words are much more common in the diagnosis database than others. As a result, some words in the unit of text from a report will match with words in many different diagnoses while others will match in far fewer diagnoses. Therefore in many cases it may be preferable to perform further analysis to identify the diagnosis matches which are most likely to be correct and/or to score and/or rank the matches to make it easier for a user to quickly identify the diagnoses with the highest probability of being correct.

Various factors may be considered by the medical record analysis system when determining which matched diagnoses are most likely to be correct. As mentioned above, one factor is how common the matched word is within the overall database of diagnoses. A match between a word in a unit of text of a report 50 with a word in a diagnosis in a database will be more significant if the word is rare than if it is common. The degree to which a word is common or rare may be determined mathematically from the frequency with which the word occurs in the diagnostic database. For example, this frequency may be represented numerically as the actual number of times the word occurs within the entire diagnostic database, though other numerical measures of frequency within the database may alternatively be used. For example, the medical record analysis system may not only factor in the number of times a word occurs in the diagnostic database but also the total number of words in the diagnostic database. This total number of words may count each word, including repeats of the same word, or may alternatively exclude repeats of the same word, when they occur within the same diagnosis. In such a method, a word that occurs in many diagnoses would have a high frequency score. However, a match of such a word in a unit of text of an exam report 50 (or reason for exam or post exam encounter report) and a diagnosis would be less specific and would be less likely to indicate a correct match. Conversely, a match between words having a low frequency score would be more likely to indicate a correct match. Therefore, the medical record analysis system may use the frequency of a word within the database as a factor in ranking the likelihood that a match between a report phrase and a diagnosis is correct. The word frequency value for each word in the database of diagnoses may be calculated and stored by the medical record analysis system. In such a system, the word frequency value would need to be updated only when the diagnosis database is changed. Alternatively, the medical record analysis system could calculate the word frequency value for each word in the report (or exam order) as part of the report or exam order analysis.

Likewise, the number of words that match between a unit of text from an exam report 50 (or exam order or post exam encounter report) and a diagnosis from the diagnosis database can also be used as a factor by the medical record analysis system when ranking the likelihood that a matched diagnosis is correct. That is, the higher the number of words that match between the unit of text from the exam report 50 and the diagnosis from the diagnosis database, the more likely the matched diagnosis is correct. In contrast, the lower the number of words that match, the less likely the matched diagnosis is correct.

Another characteristic of the matched words which the medical record analysis system may use as a factor when determining the likelihood that a matched diagnosis is correct is the position of the matched words within the unit of text from the report. When there are two or more words within a unit of text from an exam report 50 (or exam order or post exam encounter report) which match words within a diagnosis from the diagnosis database, the diagnosis is more likely to be correct when the words which match are close to each other than when they are spaced apart with non-matching words in between. The proximity of matched words to each other within a unit of text and/or within a diagnosis may therefore be factored into the ranking of the discrete diagnoses, and this may be done in several ways. For example, the medical record analysis system may factor in the number of intervening words between matched words, with a higher number of intervening words resulting in a lower ranking in the likelihood that a matched diagnosis is correct. Alternatively, the medical record analysis system may identify the number of incidences in which a matched word is directly adjacent to another matched word, with the greater the number of adjacent matched words indicating a higher likelihood that a matched diagnosis is correct. In some cases, the unit of text may have more than one grouping of adjacent matched words. For example, the unit of text may include 5 total matched words, of which 2 may be adjacent to each other and 3 may be adjacent to each other. In some embodiments, the medical record analysis system may use the number of adjacent words which is the largest group, which determining the likelihood that a diagnosis is a correct. In the example given above, this number would be 3. In other embodiments, the medical record analysis system may consider both groupings of matched words when calculating the likelihood that a diagnosis is correct.

In still another alternative, the medical record analysis system may further compare the order of the matched words in the exam report (or exam order or post exam encounter report) to the matched words in the diagnosis. When the matched words occur in the same order in the report and in the diagnosis, the diagnosis is more likely to be correct and therefore the medical record analysis system may calculate a higher likelihood that a diagnosis is correct. In this way, the medical record analysis system can further distinguish which diagnoses are most likely to be correct between a plurality of diagnoses having the same number of matched words.

In still other alternatives, the medical record analysis system may further calculate the number of words in a diagnosis phrase that did not match words in the report phrase (or exam order or post exam encounter report phrase). This value, which may be referred to as a subtract factor or unmatch factor, indicates that a match between the report phrases and a diagnosis phrase is less likely to be correct and therefore may be used to downgrade the match score of a matched diagnosis.

In step 416, using one or more of the factors discussed above, the medical record analysis system may automatically create a ranking of the diagnoses from the diagnosis database most likely to correctly correspond to the unit of text from the exam report 50 (or exam order or post exam encounter report). In some embodiments, the medical record analysis system mathematically calculates a score of the likelihood that a diagnosis is correct using a combination of one or more factors discussed above including: the number of words in the unit of text of the report that match words in a diagnosis; the total number of words in the diagnosis database; the number of words in the diagnosis; the frequency of the matched word in the diagnoses database; the proximity of matched words to each other within the unit of text of the report 50 and/or within the diagnosis; and the number of matched words within the unit of text of the report 50 which are adjacent to each other. The medical record analysis system may adjust or weight the factors so that some factors have a greater impact on the ranking of the diagnoses than others. For example, the number of words matched between the unit of text of the report 50 and the discrete diagnosis may be the most important factor in ranking the likelihood of a matched diagnosis being correct and may be given mathematically more weight than the other factors. However, since numerous diagnoses may have the same number of matched words for a given unit of text from an exam report 50 (or exam order or post exam encounter report), the medical record analysis system can use the other factors to mathematically differentiate those diagnoses most likely to be correct from among those having the same number of matched words.

An example of a mathematical formula which has been found to be particularly useful in providing a score for the likelihood that a matched diagnosis is correct is: $(b^2/a) \times c \times d$. The numerical match score generated by this formula can be used to rank the matched diagnoses, with a higher number indicating a greater likelihood that the diagnosis is correct, though the actual formula used for scoring may be modified or alternative scoring formulas may be used.

In this example, a is the number of words in the diagnosis (such as the number of words in the diagnosis after modification), b is the number of words that matched between the report phrase and the modified diagnosis, c is a number referred to as the composite word factor, and d is a number referred to as the order factor. The variables c and d are discussed further below.

The composite word factor, c, is a numerical representation of the relative value of matched words depending upon their frequency in the diagnosis database. As such, a match of a word that occurs with high frequency would be less significant and have a lower word factor value, whereas a match of an uncommon word would be more significant and have a higher word factor value. The composite word factor for a phrase, or match factor, c, may be calculated from word factor values $c1$, $c2$, etc. of each matched word as follows: $c = 1 + c_1 + c_2 \ldots$ . The individual word factors may be calculated using the following formula: $10/\sqrt{[e+10]} = c_1$ in which e is the number of times the matched word is present in the diagnostic database. This calculation may be repeated for each matched phrase to calculate an associated value of c. The composite word factor, c, may also be calculated using word factors values, or fractions of word factor values, $g_1$, $g_2$, etc. of each unmatched word as follows: $c = 1 + c_1 + c_2 \ldots - g_1 - g_2 \ldots$ .

The order factor, d, is a numerical value representing how close two matching words are to each other in a unit of text in a report 50. Matching words that are located closer to each other are more likely to indicate a correct match than those that are spaced further apart. The order factor, d, may be calculated as follows: $1 + 0.1(f-1) = d$ in which f is the number of matching words in a unit of text of a report that are directly adjacent to each other. In alternative embodiments, the medical record analysis system may calculate the order factor as a numerical value of how close two matching words are to each other and/or whether they are adjacent to each other in the diagnosis. In still another alternative embodiment, the medical record analysis system may calculate the order factor as a numerical value including both whether the two matching words are adjacent to each other in one or other of the unit of text, the diagnosis, or both, such that when they adjacent to each other in both there is a higher likelihood of a match.

The formula discussed above may be used, for each diagnosis, to calculate a score of the likelihood that the diagnosis is a correct identification of the diagnosis presented in the unit of text of the exam report 50 (or exam order or post exam encounter report). Other formulas may alternatively be used, which may include one or more of the same factors or all of the same factors discussed above. When the above formula is used, a higher value score indicates a higher likelihood that a match is correct. By recognizing that some diagnoses are more likely to be correct than others, the numerical scoring of each diagnosis allows the matched diagnoses to be ranked according to the likelihood of being a correct identification of the diagnosis in the report 50.

Steps 408 through 414 may be repeated for each unit of text of the exam report 50 (or exam order or post exam encounter report) that were segmented in step 406 until all such units of text have been analyzed. The medical record analysis system therefore generates a separate list of diagnoses for each unit of text, such that multiple lists of diagnoses are typically generated for each exam report 50. In this way the report section or sections that were segmented are fully evaluated, reducing the risk that some diagnoses could be inadvertently missed.

In step 418, the medical record analysis system may use the match score of each diagnosis to generate a ranked list of the most likely correct diagnoses which may be provided to a user. For example, the ranked list of the most likely diagnoses may be displayed on a screen 72, with the diagnoses listed in the order of likelihood of being correct, such as with the most likely correct diagnosis at the top of the list. Alternatively, the ranked list and/or the numerical values used to generate the ranked list may be stored and not displayed. In such embodiments, the stored ranked list and/or numerical values be may be available to be used or accessed at a later time.

The ranked diagnoses list, which may or may not be displayed, may include the diagnosis from the diagnosis database, either in modified form or unmodified as present in the unified set of diagnoses. The ranked diagnoses list may further include the alphanumeric code associated with each diagnosis. In addition, the ranked diagnosis list may further include the calculated match score. In some cases, the list may further include an indication whether or not the report phrase indicates the diagnosis is present or absent (that is, whether the diagnosis is a positive or negative finding). In some cases, the list may only include a maximum of a predetermined number of the top matches, such as the top 5, 10 or 20 diagnoses based on the match score and/or the medical record analysis system may allow a user to select the number of top matches to be displayed. For example, the medical record analysis system may include a threshold, which may be set by a user, indicating which diagnoses may be included on the list and below which may be excluded. The list may further include the unit of text from the report 50, either as modified by the medical record analysis system or as present in the original report 50, for which the diagnosis list has been generated, or this language may be displayed separately, associated with the list but separate from it, for the user to observe.

An example of a ranked list diagnoses display that may be provided to and displayed for a user is shown in FIG. 5. The ranked list 500 is for a negative phrase from the Impression section of a radiology report. The exact text from the radiology report 502 is displayed as well as the modified unit of text 504 used for comparison to the diagnosis database, which in this example was a modified database of ICD-10 codes and diagnoses. The first column 506 in this example is entitled ICD-10 Code and displays the alphanumeric ICD-10 Code for the diagnosis in that row. The second column 508, entitled ICD Filter Category, indicates that the category referred to as Head/Neuro could optionally be used to reduce or modify the rank of the possible diagnosis matches from the ICD-10 database for this study based on the type of study performed, a CT angiogram of the head, though in the example shown no such filtering has been selected or performed. The third column 510 is entitled Diagnosis Name and is a list of diagnoses in unmodified text form obtained by the medical record analysis system by comparing the words of the modified unit of text 504 with the words of each modified diagnosis in the diagnosis database. The fourth column 512 is entitled Num Diagnosis Words and indicates the number of words in the diagnosis text that were included in the matching analysis, while the fifth column 514 is entitled Number of Matching Words (including duplicates) and indicates the number of words that matched between the modified unit of text 504 from the report and the diagnosis in that row. The sixth column 516 is entitled Match Factor and is a numerical calculation of the frequency of the matched words within the diagnosis database, such as composite word factor c discussed above. The seventh column 518 is entitled Subtract Factor and provides a value for the number of words that did not match between the modified unit of text 304 and the diagnosis in that row. The eighth column 520 is entitled Order Factor and is a numerical calculation of the order and/or proximity of the matched words to each other, such as order factor d discussed above. The ninth column 522 is entitled Score and is a numerical value calculated using a combination of one or more values in the preceding five columns and represents the likelihood that the diagnosis in the row is a correct match for the impression line 502 of the report. In this example, most of the diagnoses had four matched words, therefore the Score information in column 522 is particularly useful. Even though most of the listed diagnoses had the same number of word matches, they are ranked and displayed with the diagnosis having the highest score, and therefore representing the most likely correct diagnosis, presented at the top, and proceeding in descending order according to the Score. The last column 524 is entitled Word Matches and shows the words that matched between the modified unit of text 504 from the report and the diagnosis in that row.

In the example shown in FIG. 5, the medical record analysis system has further identified the words of negation associated with the modified unit of text 504 from the report and indicates that the unit of text 504 is a negative diagnosis, meaning that the diagnosis was reported as not present. Whether the unit of text 504 indicates a positive or negative diagnosis, the medical record analysis system can generate the same sort of ranked list of diagnoses.

The matching process employed by the medical record analysis system may result in the identification of a large number of potential matches. However, when a large number of potential matches are produced, the usefulness of the list of matched diagnoses may be decreased. As such, the medical record analysis system may take further steps to reduce the number of matched diagnoses displayed for a user. For example, the medical record analysis system may display only a certain predefined number of matches, which would include only the matched diagnoses having the highest score. As such, the displayed matches would only be those most likely to be correct, while those with a lower probability of being correct would not be displayed. This predefined number of matches may be automatically determined by the medical record analysis system or may be selected by a user. Alternatively, the medical record analysis system may display only those matches having a score greater than a particular threshold match score, which may be set by the medical record analysis system or the user.

In some embodiments, the medical record analysis system may reduce the number of diagnoses presented to a user by eliminating diagnoses which are not possible for the type of procedure or test being reported. For example, based on the location within the body on which the procedure or test was performed, diagnoses relating to other parts of the body would not be possible and would be eliminated. For example, the list of matched diagnoses in FIG. 5 includes "injury of suprarenal arteries" while the examination performed was a head CTA. While the scoring system gave this diagnosis a low score as compared to the other matched diagnoses, the medical record analysis system could be further refined to eliminate this diagnoses based on its location in the kidneys, which could not be discovered through a head CTA. This may be implemented in a variety of ways. In some embodiments, the diagnoses listed in the diagnosis database may be categorized according to general body locations such as head, neck, chest, abdomen, pelvis, spine, upper extremity, lower extremity, etc. In addition, there may be a category such as miscellaneous or unspecified for diagnoses which are not limited to a specific location in the body. Different types of reports could similarly be categorized to the same set if general body locations. In some case, one type of report may be categorized to more than one general body location. For example, a CT of the head may be categorized to both the head and the neck, since diagnoses in both the head and the neck could be identified using a CT of the head. The matching process may then be performed as described elsewhere, but only using the diagnoses which are categorized to the body location or locations corresponding to the locations for the exam on which the report is based, as well as diagnoses in the miscellaneous category for which there is no specific location.

The list of matched diagnoses may be used in many ways. For example, the list may be used by individuals such as medical coders who normally perform the task of reviewing medical records to identify the appropriate standardized diagnostic and procedure codes for purposes of obtaining reimbursement from medical insurance providers. Without the use of the medical record analysis systems described herein, such medical coders must read the records and search through extremely long lists of codes to find the correct diagnosis and code. Therefore, the process is time-consuming and errors and omissions are difficult to avoid. In addition, a medical coder may select a code which is overly generic in order to speed up the process rather than continuing to search for the most accurate and specific code. However, when using the medical record analysis systems described herein, the medical coders can be automatically presented with a much shorter list of the diagnoses and codes which are most likely to be correct and more specific.

Because the list of matched diagnoses and codes may be ranked with the diagnoses and codes that are most likely to be correct on top, the medical coder can quickly identify the correct diagnosis and code by reviewing from the top and down the list until seeing the correct diagnosis and code. The medical coder can then select this diagnosis and code, such as by clicking on it, and it may be automatically entered into the billing system. The process is therefore much quicker and easier than the traditional method of searching an exhaustive list.

Furthermore, the medical record analysis system promotes the identification of more specific and accurate matches. By shortening the list of likely diagnosis, the medical coder can easily review the most likely matches to identify the most accurate and specific diagnosis, rather than conducting an exhaustive and time-consuming search. In some cases, the medical record analysis system may even rank the most specific diagnosis higher than more generic diagnosis, further improving the likelihood of an accurate and specific selection by the medical coder.

The process of medical coding is further enhanced by sectioning the report into discrete units of text. In some embodiments, the medical coder can see the unit of text from the report and the list of matched diagnoses and codes together on the display, making it easy to read the phrase and select the most correct diagnosis and code. In addition, because the medical record analysis system automatically breaks the report into discrete units, it increases the likelihood that the medical coder will identify all diagnoses present in the report. Without the medical record analysis system, the medical coder might read the report and glean out the primary or most significant diagnoses, but other diagnoses and incidental findings mentioned in the report might be unintentionally overlooked. However, because the medical record analysis system automatically segments the relevant portions of the report into units of text and matches each unit of text to the diagnostic database to generate a list of diagnoses, information in the report is much less likely to be accidently omitted. Rather, the medical coder is more likely to identify all diagnoses presented in the report.

In some embodiments, the medical record analysis system may be used for monitoring the quality of reports or for quality improvement. For example, in some embodiments the medical record analysis system is a component of, or is in electronic communication with, a medical record system such as medical records 48. The medical record system may include information about a patient's hospital stay including discrete clinical data elements which may be in the form of non-free-text data fitting within a specification such as an alphanumeric code (such as an ICD-10 code), date(s), times, weights, ages, etc. Such discrete clinical data elements may include the patient's final diagnoses upon discharge which may be in the form of an alphanumeric code. In some such embodiments, the medical record analysis system may upload a document including the patient's final diagnosis for the same hospital stay. For example, the patient's electronic record on the medical service provider system 40 may include a plurality of databases of information including database tables with discrete fields. One such field may be exam reports 50 while others in 48 may include the encounter diagnoses (for a hospital stay or clinic appointment, for example) which may be the post exam encounter diagnoses, and these may be directly accessed and extracted by the medical record analysis system. Other discrete fields which may likewise be accessed and extracted as supplemental databases of the medical service provider system 40 include the patient's age, the report provider (such as the reading radiologist, as discussed above), the study type, etc., The medical record analysis system may then compare the diagnoses generated from the exam report 50 as described above to the patient's final diagnosis such as the post exam encounter diagnoses from the medical record. This may be done by comparing the alphanumeric codes of the post exam encounter diagnosis from a patient's medical record with the alphanumeric codes of the matched diagnoses list or lists generated by the medical record analysis system for the report 50. If the post exam encounter diagnosis from the medical service provider system matches a diagnosis generated by the medical record analysis system for the report 50 matches the final diagnosis for the patient, this can be considered confirmation that the physician's interpretation of the study presented in the report 50 was correct. The post exam encounter diagnosis will typically include many diagnoses that are unrelated to the exam report, and not all diagnoses generated by the medical record analysis system for the exam report 50 may be found in the post exam encounter diagnoses every time. Nevertheless, when a post exam encounter diagnosis matches a diagnosis generated by the medical record analysis system, this suggests that the finding in the report was accurate and further suggests that the medical record analysis system correctly interpreted the exam report 50. As such, the medical record analysis system can be used to evaluate the relative accuracy of a provider overall, in specific types of studies, during a certain time period, etc., as selected by the user of the medical record analysis system. For example, the medical record analysis system could include a database of exam reports 50, or the exam reports 50 could be included within the medical record system accessible by the medical record analysis system described herein. In this way, a user could query the medical record analysis system for an accuracy score for an individual provider.

When receiving such a query, the medical record analysis system may search for exam reports 50 (all reports or all of a certain type of report or reports during a certain time period, for example) created by a specific physician, either within the report database or within the medical records 48 or in the generated data 28 if the reports have been previously analyzed.

The medical record analysis system may then apply the steps of determining the diagnosis from the exam report 50 as described above. Alternatively, the medical record analysis system may have previously analyzed the exam reports 50 and generated diagnoses, which may have been confirmed by a medical coder, and the medical record analysis system may access this information directly rather than the original reports 50. The medical record analysis system may then access the encounter diagnoses from the medical record of the medical service provider system, though these may have been previously imported into the medical record analysis system generated data database 28. For each exam report 50, the medical record analysis system may then compare the diagnoses generated by the medical record analysis system from the exam report 50 to the final diagnosis from the discharge summary or the post exam encounter report. The medical record analysis system may then generate a score based upon the number of diagnoses in the report 50 that match the post exam encounter diagnoses. The accuracy scores for each report 50 may be aggregated to obtain an overall score for the provider. Alternatively, the score may be limited to particular studies (such as only MRIs, only MRIs of the head, etc.), to specific date ranges, etc., as directed by the user query. This information may be used to track provider performance, to alert a supervisor or other user of the medical record analysis system to any provider whose accuracy scores are lower than other physicians indicating a possible problem, and to participate in quality improvement as required by insurance or government regulations or incentives.

Since any or all of the reason for exam, the exam report diagnoses, and the post exam encounter diagnoses may be generated by the medical record analysis system and/or by coder or other individual (ordering physicians, radiologists, etc,) and may use the same standard alphanumeric code system, they can be compared using the alphanumeric codes of the diagnoses. The alphanumeric codes may be considered to match when all of the alphanumeric code matches or when less than all of the code matches. For example, the medical record analysis system may conclude that there is a match when the codes are identical. Alternatively, the medical record analysis system may conclude that there is a match when the first 2, 3, 4, 5, 6, 7, 8, and/or 9 alphanumeric characters match. In some embodiments, a user may direct the medical record analysis system to identify matches and may specify the how many of the first alphanumeric characters must be identical to be considered a match, while in other embodiments, the number of character which must be identical may be preset, such as to the first 5 or the first 6 characters. In many standardized sets of diagnoses and alphanumeric codes, such as the ICD system, the first numbers (leftmost characters in a code) represent a more generic diagnosis, while the subsequent numbers identify the diagnosis with increasing specificity. It may therefore be useful to identify matches at a more generic level by specifying that a smaller number of characters must match, or at a more specific level by specifying that a greater number or even that all of the characters must match, in order for an encounter diagnosis to be considered a match for a diagnosis generated by the medical record analysis system.

When evaluating provider performance in generating exam reports 50, the speed with which the provider generates reports exam 50 is also important, but speed can be affected by the complexity of the study on which the provider is reporting. For example, the time required for a provider to analyze a study and generate a report will vary depending upon the nature of the patient population. For example, an image (X-ray, MRI, etc.) of a healthy individual is more likely to be normal, or may show one common type of abnormality, such as a bone fracture due to trauma, which the study was performed to detect. Because the study is common, with routine findings, a provider can review such a study and generate a report relatively quickly. Such studies are likely to be more common in an outpatient, community radiology center, for example. In contrast, images of patients with multiple medical problems or more complex problems are more difficult and time consuming to analyze. It will take much more time for a provider to generate a report on such patients. Patients with complex medical problems are more likely to seek care from providers with expertise in complex medical situations and specifically expertise in their conditions, such as at the hospitals of academic institutions that conduct research. As a result, providers at such institutions may be highly skilled but nevertheless they may appear to be slow or inefficient in generating reports due to the complex nature of the patient population.

To make a more accurate assessment of provider performance, the medical record analysis system may be used to rank reports according to complexity. This could be done in a variety of ways. For example, the medical record analysis system could assign a complexity score to the exam report 50 based upon the number of diagnoses identified, weighting of the number of positive and negative findings, the complexity of the identified diagnoses, or other factors or a combination of factors. In some embodiments, the complexity of the identified diagnoses may be determined from morbidity and mortality data. For example, the Centers for Disease Control publishes data regarding the leading causes of death by ICD-10 code, or the Center for Medicare & Medicaid Services publishes models using a Hierarchical Condition Category to allow calculation of risks in correlation with ICD-10 diagnosis codes. Information such as this may be used to score the complexity of diagnoses, which may in turn be used to score the complexity of a report 50.

The information obtained by the medical record analysis system through analyzing the exam reports 50 (or exam orders or post exam encounter reports) and/or from the medical records 48 of the medical service provider system 40 may include the type of study performed, location on the patient body on which the study was performed, patient age and gender, date of study, diagnoses, etc. The medical record analysis system may create a database including some or all of this information, such as the generated data 28 in FIG. 1, which may be stored and may grow as new studies are analyzed. This database may be used by users such as researchers who may query the medical record analysis system to identify studies according to various parameters stored in the database. For example, a researcher may be interested in a combination of a certain disease (diagnosis) and type of radiological study. Without this medical record analysis system, the user would have to manually review study reports to locate the studies that would be useful for research purposes. However, with the database of analyzed report information, the user can query the medical record analysis system for any one or more parameters stored by the medical record analysis system, in particular generated diagnosis codes, to generate a list of studies that suit the user's needs.

In some embodiments, the medical record analysis system may provide a reason for exam when this portion of an order is left blank, and this may be performed automatically or at the direction of a user. The medical record analysis system may analyze the exam order according to the steps shown in FIG. 4, but instead of analyzing an exam report is analyzes an exam order. After identifying sections of the exam order, the system may identify the reason for exam section and determine whether or not it includes any text or alphanumeric code. If no text is included in a field denoted as the reason for exam, the system may perform various steps to identify diagnoses that could be the reason for exam. For example, the system may analyze other discrete data elements of the order, such as free-text comments or multiple-choice order instructions, to identify diagnoses according to the methods described herein. Alternatively, the system could search the medical record of the patient to identify a reason for exam on a previous exam order. Such previous exam orders could be restricted to exams of the same body location and/or of the same type. In still other alternatives, the system could identify a diagnosis from the exam report which could be the reason for exam. Finally, the system could search the medical record of the patient for a post exam encounter diagnosis or discharge diagnosis which could be a reason for exam. In some embodiments, the system may conduct each of the preceding steps in a defined order, such as the order listed above, or may conduct all of the preceding steps and identify a reason for examination that is consistent and specific from the sets of diagnoses identified in the previous steps. The system may automatically select an identified diagnosis or previous reason for exam and insert it into the exam order as the reason for exam. Alternatively, the system may present one or more identified diagnoses or reasons for exam to an individual and request the individual to select and/or confirm the reason for exam for the order. In these ways, the reason for exam section of the exam order can be completed to provide more information to the reading radiologist and as necessary for reimbursement.

In some embodiments, the medical record analysis system may include a dictation system for receiving dictated reports to provide live feedback and/or requests for information to a provider creating a report. This dictation system may include a user interface including a microphone for a provider to dictate a report and language recognition programming to recognize the spoken words and convert them to text. The dictated report may be received by the dictation system and the language recognition programming may simultaneously or nearly simultaneously convert the dictation into text. The medical record analysis system may then analyze this text using the methods described previously herein to identify the type of report, the diagnoses, and other information. It may then use this information to generate questions or prompts to the dictating provider. For example, the medical record analysis system may determine the most likely diagnosis or a list of the most likely diagnoses from the diagnosis database and present them to the provider, such as on the computer screen, with a request for the provider to confirm or select the correct diagnosis. As another example, some diagnoses require certain information to be provided by the provider in order for the diagnosis to be reimbursed by or to comply with a standard of care. When such a diagnosis is identified by the medical record analysis system, it may immediately generate a request for this information to the provider. Because the medical record analysis system is analyzing the report while it is being dictated, these requests may be presented to the provider while he or she is still performing the dictation and/or immediately after completing the dictation, making it easy for the provider to identify the correct response or to dictate or input the additional requested information. In contrast, when a provider is contacted later with requests such as these, the provider may no longer remember the study and determining the correct response requires much more of the provider's time and effort.

In the foregoing description, the inventions have been described with reference to specific embodiments. However, it may be understood that various modifications and changes may be made without departing from the scope of the inventions.

The invention claimed is:

1. A computer implemented method for analysis of radiologic imaging orders, the method comprising:
using a processor, executing computer readable instructions stored in non-transitory computer readable media to perform the steps of:
   a. receiving a query for analysis of radiologic imaging orders of a first group of patients who all underwent radiologic imaging exams of the same type, wherein the radiologic imaging exams resulted in radiologic exam reports, and wherein the radiologic imaging exam orders were used to order the radiologic imaging exams;
   b. identifying reason for exam codes for the radiologic imaging orders of the first group of patients;
   c. identifying exam report diagnosis codes for the radiologic exam reports of the first group of patients;
   d. calculating a value corresponding to a frequency of the exam report diagnosis codes occurring in association with the reason for exam codes for the first group of patients;
   e. calculating a standard value corresponding to a frequency of the exam report diagnosis codes occurring in association with the reason for exam codes for a second group of patients wherein the second group of patients all underwent the same type of radiologic imaging exam as the first group of patients, and wherein the second group of patients is sufficiently large for a statistical determination of the frequency of the second group as an ideal frequency value; and
   f. comparing the value calculated in step d to the standard value calculated in step e;
   wherein the radiologic imaging orders and radiologic exam reports of the first and second groups of patients are within electronic records of a healthcare provider network,
   wherein the steps are performed continuously to monitor for a problem with ordering of radiologic imaging exams within the healthcare provider network.

2. The computer implemented method of claim 1 wherein, for one or more of the radiologic imaging exam reports, identifying exam report diagnosis codes in radiologic exam reports comprises:
   i. segmenting the radiologic exam report into a plurality of units of text;
   ii. comparing a first unit of text to a plurality of phrases contained in a database to identify one or more matched phrases, wherein a matched phrase is identified when a phrase in the database has one or more words that are the same as one or more words in the first modified unit of text; and
   iii. repeating steps i-ii for a second unit of text.

3. The method of claim 2 wherein the first group of patients is identified by geographic location, clinical provider or providers and/or type of imaging study or studies.

4. The method of claim 1 wherein the standard value in step e comprises a threshold value.

5. The method of claim 1 wherein the value calculated in step d comprises a frequency with which one particular reason for exam code was associated with one particular exam report diagnosis code within the group of patients.

6. The method of claim 5 wherein the type of radiologic exam comprises an MRI of the head and wherein the reason for exam code corresponds to a headache.

7. The method of claim 1 wherein the value calculated in step d comprises a frequency with which one or more particular reason for exam codes present on radiologic imaging exams resulted in one or more particular exam report diagnosis codes within the group of patients.

8. The method of claim 1 wherein receiving a query in step a comprises receiving a query from a user, the method further comprising:
   g. based on the comparison of step f, notifying the user of an actual problem or a potential problem with the radiologic imaging exam orders for the first group of patients, wherein the actual problem or the potential problem comprises over utilization of the radiologic imaging exam type or ordering an incorrect type of radiologic imaging exam.

9. The method of claim 1 wherein step e comprises:
   i. identifying reason for exam codes for the radiologic imaging orders for the second group of patients;

ii. identifying exam report diagnosis codes for the radiologic exam reports for the second group of patients; and
iii. calculating the standard value corresponding to a frequency of the exam report diagnosis codes occurring in association with the reason for exam codes for the second group of patients.

10. A computer implemented method for analysis of radiologic imaging orders, the method comprising:
using a processor, executing computer readable instructions stored in non-transitory computer readable media to perform the steps of:
a. receiving a query for analysis of radiologic imaging orders of a first group of patients who all underwent radiologic imaging exams of the same type, the radiologic imaging exams resulting in radiologic exam reports, wherein the radiologic imaging exam orders were used to order the radiologic imaging exams;
b. identifying reason for exam codes for the radiologic imaging orders of the first group of patients;
c. identifying exam report diagnosis codes for the radiologic exam reports of the second group of patients by performing the steps of:
i. segmenting the radiologic exam report into a plurality of units of text;
ii. comparing a first unit of text to a plurality of phrases contained in a database to identify one or more matched phrases, wherein a matched phrase is identified when a phrase in the database has one or more words that are the same as one or more words in the first modified unit of text; and
iii. repeating steps i-ii for a second unit of text
d. calculating a value corresponding to a frequency of the exam report diagnosis codes occurring in association with the reason for exam codes for the first group of patients; and
e. calculating a standard value corresponding to a frequency of the exam report diagnosis codes occurring in association with the reason for exam codes for a second group of patients, wherein the second group of patients all underwent the same type of radiologic imaging exam as the first group of patients, and wherein the second group of patients is sufficiently large for a statistical determination of the frequency of the second group as an ideal frequency;
f. comparing the value calculated in step d to the standard value calculated in step e;
wherein the radiologic imaging orders and radiologic exam reports of the first and second groups of patients are within electronic records of a healthcare provider network, and
wherein the steps are performed continuously to monitor for a problem with ordering of radiologic imaging exams within the healthcare provider network.

11. The method of claim 10 wherein the query identifies the first group of patients as all having a same reason for exam.

12. The method of claim 10 wherein receiving a query in step a comprises receiving a query from a user, the method further comprising:
g. based on the comparison of step f, notifying the user of an actual problem or a potential problem with the radiologic imaging exam orders for the group of patients.

13. The method of claim 12 wherein the actual problem or the potential problem comprises over utilization of a radiologic imaging exam type.

14. The method of claim 12 wherein the actual problem or the potential problem comprises ordering incorrect radiologic imaging exams.

15. A computer implemented method for analysis of radiologic imaging orders, the method comprising:
using a processor, executing computer readable instructions stored in non-transitory computer readable media to perform the steps of:
a. receiving a query from a user for analysis of radiologic imaging orders of a first group of patients who underwent radiologic imaging exams resulting in radiologic exam reports, wherein the radiologic imaging exam orders were used to order the radiologic imaging exams;
b. identifying reason for exam codes for the radiologic imaging orders of the first group of patients;
c. identifying exam report diagnosis codes for the radiologic exam reports of the first group of patients;
d. calculating a value corresponding to a frequency of the exam report diagnosis codes occurring in association with the reason for exam codes for the first group of patients;
e. calculating a standard value corresponding to a frequency of the exam report diagnosis codes occurring in association with the reason for exam codes for a second group of patients wherein the second group of patients is sufficiently large for a statistical determination of the frequency of the second group as an ideal frequency;
f. comparing the value calculated in step d to the standard value calculated in step e; and
g. based on the comparison of step f, notifying the user of whether or not there is an actual problem or a potential problem with the radiologic imaging exam orders for the first group of patients;
wherein the radiologic imaging orders and radiologic exam reports of the first and second groups of patients are within electronic records of a healthcare provider network, and
wherein the steps are performed continuously to monitor for a problem with ordering of radiologic imaging exams within the healthcare provider network.

16. The method of claim 15 wherein the actual problem or the potential problem comprises over utilization of a radiologic imaging exam type within the radiologic exams performed on the group of patients.

17. The method of claim 15 wherein the actual or the potential problem comprises ordering incorrect radiologic imaging exams within the radiologic exams performed on the first group of patients.

18. The method of claim 15 wherein step c identifying exam report diagnosis codes for the radiologic exam reports comprises performing steps:
i. segmenting the radiologic exam report into a plurality of units of text;
ii. comparing a first unit of text to a plurality of phrases contained in a database to identify one or more matched phrases, wherein a matched phrase is identified when a phrase in the database has one or more words that are the same as one or more words in the first modified unit of text; and
iii. repeating steps i-ii for a second unit of text.

19. The method of claim 18 wherein steps i-iii are performed by the processor in response to the query of step a.

20. The method of claim 18 wherein steps i-iii are performed prior to the query, either by the processor or by a second processor, and wherein exam result codes resulting from steps i-iii are stored in digital memory and accessed by the processor in step c.

* * * * *